(12) United States Patent
Ishii

(10) Patent No.: US 6,652,901 B2
(45) Date of Patent: Nov. 25, 2003

(54) SWEETENER COMPOSITIONS AND USES THEREOF

(75) Inventor: Shoichi Ishii, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/115,242

(22) Filed: Apr. 4, 2002

(65) Prior Publication Data

US 2003/0059511 A1 Mar. 27, 2003

Related U.S. Application Data

(63) Continuation of application No. PCT/JP00/06628, filed on Sep. 26, 2000.

(30) Foreign Application Priority Data

| Oct. 4, 1999 | (JP) | ............................................ | 11-283505 |
| Oct. 4, 1999 | (JP) | ............................................ | 11-283506 |
| Oct. 5, 1999 | (JP) | ............................................ | 11-284346 |

(51) Int. Cl.⁷ .............................................. A23L 1/236
(52) U.S. Cl. ......................... 426/548; 560/41; 562/433
(58) Field of Search ................................ 426/548, 590; 560/40, 41; 562/409, 433, 442, 450

(56) References Cited

U.S. PATENT DOCUMENTS

| 4,158,068 A | 6/1979 | Von Rymon Lipinski et al. |
| 5,480,668 A | * 1/1996 | Nofre et al. ................. 426/548 |

FOREIGN PATENT DOCUMENTS

| EP | 1088829 A1 | 4/2001 |
| WO | 98/39979 | 9/1998 |
| WO | 99/30577 | 6/1999 |

OTHER PUBLICATIONS

WO 00/00508 A1, U.S. patent application Ser. No. 09/736,149 filed Mar. 16, 2001. (English Abstract).

N. Ayya, et al., Chemical Senses, vol. 17, No. 3, pp. 245–259, XP–000991203, "Quantitative and Qualitative Evaluation of High–Intensity Sweeteners and Sweetener Mixtures", 1992.

* cited by examiner

*Primary Examiner*—Leslie Wong
(74) *Attorney, Agent, or Firm*—Oblon, Spivak, McClelland, Maier & Neustadt, P.C.

(57) ABSTRACT

The present invention provides compositions containing one or more aspartyl dipeptide derivatives represented by formulas (1) and/or (2) mixed with another high intensity sweetner, such Aspartame, sugar, sugar alcohol, and oligosaccharide; food, beverages, and/or medicinal products containing these compositions, methods of using the compositions to impart sweetness in food, beverages, and/or medicinal products to impart sweetness or suppress a bitter taste; and methods of making the compositions and products.

17 Claims, No Drawings

SWEETENER COMPOSITIONS AND USES THEREOF

CROSS-REFERENCE TO RELATED APPLICATIONS

The present application is a continuation application of PCT/JP00/06628 filed Sep. 26, 2000, the entire contents of which are incorporated by reference. This application also claims priority to Japanese Patent Applications 11-283505 filed Oct. 4, 1999, 11-283506 filed Oct. 4, 1999, and 11-284346 filed Oct. 5, 1999, the contents of which priority applications is incorporated by reference.

FIELD OF THE INVENTION

The present invention relates to a novel sweetener composition. In particular, a sweetener composition (or taste modifiers) with a high intensity sweetness, which comprises a specific aspartyl dipeptide ester compound, for example, N-[N-[3-(3-hydroxy-4-methoxyphenyl) propyl]-L-α-aspartyl]-L-phenylalanine 1-methyl ester and an another sweetener with a high intensity sweetness, for example, Aspartame, sugar, sugar alcohol, oligosaccharide (such as sucrose), whereby the combination provides an improved sweetness quality from said derivative. The invention also provides sweeteners, foods, beverages or other products, which benefit from having a sweet taste (for example, medicinal products), containing the sweetener composition therein. The present invention also provides a method of imparting a sweet taste into a food, beverage, or other sweetened product using the above sweetener composition.

BACKGROUND OF THE INVENTION

It has been reported that the sweetness intensity of Neotame which is a sweetener with a high intensity sweetness is 10000 times that of sucrose by weight (refer to Japanese Patent Kohyo Publication JP-A-8-503206), and the sweetness intensity of Aspartame is 200 times that of sucrose by weight (refer to Japanese Patent Kokoku Publication JP-B-47-31031). These sweeteners have been commercially used and research for additional applications is ongoing. While many other sweeteners with a high intensity sweetness have been proposed, these sweeteners have many practical problems for use.

Therefore, a sweetener with a high intense sweetness, which is different from the sweetness of conventional sweeteners is in demand, preferably such a sweetener should possess a high intensity sweetness, with excellent sweeteness quality, and physical properties (such as stability).

Regarding taste modifiers, which suppress bitter tastes, numerous attempts to develop a suitable product and methods of employing the taste modifiers have been investigated. A need for such taste modifiers exists in formulating medicines or pharmaceuticals, which often contain ingredients imparting a bitter taste as an effective ingredients. Thus, there is a need in the area pharmaceuticals to remove and/or suppress the bitter taste; and to maintain the effect for a long time (refer to Japanese Patent Kokai Publication JP-A-6-298668).

To remove and/or suppress such bitter tastes sugar coatings or other encapsulation methods are typically employed. Where such a suppression or removal effect is required in a liquid formulation typically taste modifiers are added in high concentrations due to the difficulty of stably coating a liquid compared to a solid. Recently, it has been proposed to suppress the bitter taste by adding lecithin. However, suppression of the bitter taste is not sufficient by these methods and the effect is weakened due to decomposition during storage in a solution. Moreover, the addition of sugar is not suitable for calorie-controlled diet regimens, such as those diets for diabetic patients. Likewise, in preparing formulations for administration to babies and children, who are difficult when it comes to administrating tablets or granular preparations, liquid formulations or dry syrups, which are dissolved prior to use, are typically employed.

It has also been proposed to add lecithin for the same effect as discussed for medicine/pharmaceuticals discussed above in addressing problems with food products, such as bitter tastes due to peptides and amino acids containing hydrolyzed vegetable or animal protein, fruit juices, minerals, etc., which are added for enrichment of nutrition sweeteners, adsorbents, inclusion compounds, enzymes and/or organic acids.

However, the above methods often fail because of the difficultly in obtaining a sufficient effect, which also depends on the substance imparting the bitter taste. Likewise, minimizing the use of sweeteners, such as sugar, in calorie controlled diet regimens fails to provide the bitter taste suppressing effect, for example when using Glycyrrhizin. Moreover, the sweeteners present in an aqueous solution have the problem of decomposition.

As a result of research to develop a sweet substance with a high intense sweetness, the present inventors have found that an aspartyl dipeptide ester derivative represented by formula (2) had a high intense sweetness and was useful as a sweetener.

According to further study by the present inventor, although the magnification intensity of sweetness of the derivative is extremely high, the onset of taste (the early taste) is very weak compared to that of sucrose, whereas the lingering taste (the later taste) is felt very strongly. Therefore, a need exists to develop a sweetener composition with a high intense sweetness having a good and well-balanced sweetness quality for preparing a sweetener.

SUMMARY OF THE INVENTION

Thus, an object of the present invention to provide a sweetener composition having a superior sweetness quality with good balance with respect to the onset of the taste.

It is another object of the present invention to develop a taste modifier, which can be widely applied to food, beverages, and medicines and which can have a superior effect in an aqueous solution.

It is another object of the present invention to develop a taste modifier, which can remove bitter tastes, exhibit the bitter taste suppression effect for a long time, without undesirable effects, such as unstablility, viscosity, and degradation of quality such as browning during the storage.

DETAILED DESCRIPTION OF THE INVENTION

The present inventor has studied eagerly to solve the problem described above and have found that a well-balanced sweetener composition can be obtained by combining aspartyl dipeptide ester derivatives and another sweetener with a high intense sweetness. This well-balanced sweetener composition provides the a stronger onset of the taste and a weaker lingering taste.

The present inventors have also found that a sweetener composition having a well-balanced sweetness quality is obtained by combining the aspartyl dipeptide ester derivatives and at least one of a sugar, sugar alcohol and/or oligosaccharide.

The present inventors have also found that the problems associated with the taste modifiers described above can be solved with and have found that the derivatives described herein can remove or suppress the bitter taste, and maintain this effect for a long time, without undesirable effects typically associated with such taste modifiers when employed in food, beverages, and/or medicines.

One embodiment of the present invention is a sweetener composition with a high intense sweetness comprising an aspartyl dipeptide ester derivative or a salt thereof, which is represented by formula (2), preferably formula (1), mixed with an another sweetener with a high intense sweetness, wherein the sweetness quality from said derivative is improved.

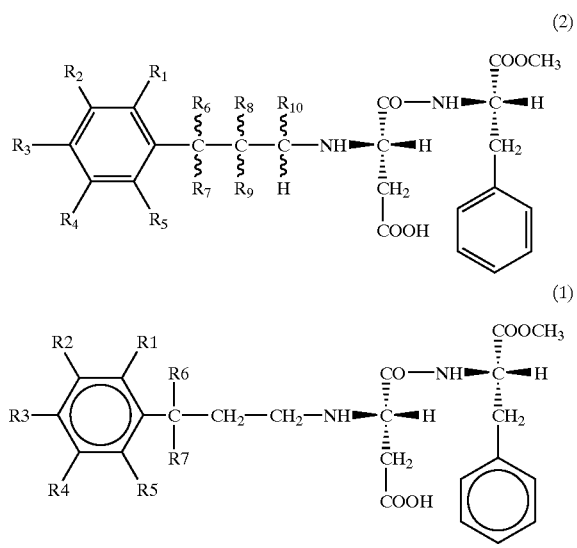

In the above formulas (1) and (2) $R_1$, $R_2$, $R_3$, $R_4$ and $R_5$ are independent from each other, and can be a hydrogen atom, a hydroxyl group, an alkoxy group having 1 to 3 carbon atoms (methoxy, ethoxy, n-propoxy, etc.), an alkyl group having 1 to 3 carbon atoms (methyl, ethyl, n-propyl, etc.) and a hydroxyalkyloxy group having 2 or 3 carbon atoms ($O(CH_2)_2OH$, $OCH_2CH(OH)CH_3$, etc.), and $R_1$ and $R_2$, or $R_2$ and $R_3$ can be combined to form a methylene dioxy group ($OCH_2O$); $R_6$, $R_7$, $R_8$, $R_9$ and $R_{10}$ are independent from each other, and each is a hydrogen atom or an alkyl group having 1 to 3 carbon atoms (methyl, ethyl, isopropyl and etc.), and where any two of $R_6$, $R_7$, $R_8$, $R_9$ and $R_{10}$ may be combined together to form an alkylene group having 1 to 5 carbon atoms ($CH_2$, $CH_2CH_2$, $CH_2CH_2CH_2$ and etc.). When $R_6$ and $R_7$, or $R_8$ and $R_9$ are different substituents, or $R_{10}$ is a substituent other than a hydrogen atom, the configuration of the carbon atom to which these substituents ($R_6$ and $R_7$, $R_8$ and $R_9$ or $R_{10}$) are linked, has no restriction, and may be in (R), (S), (RS) configurations or a mixture thereof. In addition, the wiggly line representing the bonds of $R_6$ to $R_{10}$, and an hydrogen atom with a carbon atom in formula (2) mean that the direction of the bond is not specified.

When $R_6$ is a hydrogen atom or a methyl group, $R_1$, $R_2$, $R_3$, $R_4$, $R_5$, $R_7$, $R_8$, $R_9$ and $R_{10}$ are not hydrogen atoms. The derivative where $R_2$ or $R_4$ denote a methoxy group, $R_3$ denotes a hydroxyl group, $R_{10}$ denotes a hydrogen atom or a methyl group, $R_1$, $R_4$, $R_5$, $R_6$, $R_7$, $R_8$, and $R_9$ are not hydrogen atoms. In a preferred embodiments the aspartyl dipeptide ester derivative where $R_8$, $R_9$ and $R_{10}$ are hydrogens is used; in the derivative of the formula (2) (a) $R_3$ is a hydroxyl group or a methoxy group, and $R_4$ and $R_5$ are hydrogens; (b) $R_1$ is a hydroxyl group (c) R is a hydrogen atom (d) $R_2$, $R_6$ and $R_7$ hydrogens, (e) $R_2$ is a hydrogen atom, a hydroxyl group or a methyl group.

In another preferred embodiment, the derivatives of formula (2), where $R_8$, $R_9$ and $R_{10}$ are hydrogens are listed in the following Table 1:

TABLE 1

| Derivative No. | $R_1$ | $R_2$ | $R_3$ | $R_4$ | $R_5$ | $R_6$ | $R_7$ |
|---|---|---|---|---|---|---|---|
| 1 | H | OH | $OCH_3$ | H | H | H | H |
| 2 | H | H | $OCH_3$ | H | H | H | H |
| 3 | H | OH | $OCH_3$ | H | H | $CH_3$ | $CH_3$ |
| 4 | H | $CH_3$ | OH | H | H | $CH_3$ | $CH_3$ |
| 5 | H | H | $OCH_3$ | H | H | $CH_3$ | $CH_3$ |
| 6 | H | H | OH | H | H | $CH_3$ | $CH_3$ |
| 7 | OH | H | $OCH_3$ | H | H | H | H |
| 8 | H | $CH_3$ | OH | H | H | H | H |
| 9 | OH | H | OH | H | H | H | H |

The sweetness intensity of the aspartyl dipeptide ester derivative used for the present invention can be more than 4,000 times that of sucrose.

The aspartyl dipeptide derivatives can also be employed in the salt form, or example, edible salts form such as hydrochloride salts, sodium salts, potassium salts, ammonium salts, calcium salts and magnesium salts and etc.

A sweetener, food and drink and other sweetened product containing the sweetener compositions described herein are also contained in the present invention.

Another embodiment of the present invention is a sweetener composition containing an aspartyl dipeptide ester derivative (which may be in the salt form) represented formula (2), inclusive of formula (1), and at least one of a sugar, sugar alcohol and/or an oligosaccharide, which combination provides an improved sweetness quality from the derivative. Mixtures of the aspartyl dipeptide ester derivatives may also be employed.

Another embodiment of the present invention is a taste modifier containing an aspartyl dipeptide ester derivative (which may be in the salt form) represented by formula (2), inclusive of formula (1). Mixtures of the aspartyl dipeptide ester derivatives may be employed in such taste modifiers.

A product such as a food, a beverage and/or a medicine having such a taste modifier and having a removed or suppressed bitter taste is included in the present invention. The taste modifiers are particularly applicable to products containing an amino acid, a peptide, a quinine, caffeine and a mineral, which have an inherent bitter taste.

The amount of the aspartyl dipeptide ester derivative (one or mixture of two or more) in a product, such as a food, beverage, and/or a medicine, is in an amount of from 0.2 ppm to 10000 ppm by weight.

The aspartyl dipeptide derivatives of the present invention can be used in a liquid formulation, whereby it is stable and exhibits excellent sweetness.

The aspartyl dipeptide ester derivatives of the present invention can be synthesized by reductive alklyation of Aspartame with 3-phenylpropionaldehyde derivative, cinnamaldehyde derivative or (2-phenylethyl) alkyl ketone derivative having various substituents on the phenyl group and one or two alkyl substituents on the main chain; and a reducing agent (e.g., hydrogen/palladium carbon catalyst).

Alternatively, the derivatives can be obtained by a process whereby an Aspartame derivative having a protecting group in place of the carboxyl group at the β position (for example, β-o-benzyl-α-L-aspartyl-L-amino acid methyl ester), which can be obtained by ordinary peptide synthesis method (Izumiya et al., Fundamentals and experiments of peptide synthesis: Maruzen, published on 1985.1.20), is reductively alkylated with the 3-phenylpropionaldehyde derivative, cinnamaldehyde derivative or (2-phenylethyl) alkyl ketone derivative described above; and a reducing agent (e.g., $NaB(OAc)_3H$) (A. F. Abdel-Magid et al., Tetrahedron Letters, 31, 5595 (1990)), and then removing the protecting group, or by saturating the unsaturated bond with a reducing agent, if necessary. Instead of the 3-phenylpropionaldehyde derivative, cinnamaldehyde derivative or (2-phenylethyl) alkyl ketone derivative, an acetal or ketal derivative thereof can be used as an aldehyde or ketone component for the reductive alkylation.

These derivatives can be easily produced by known peptide synthesis method as shown above, or according to the production examples described herein.

The other sweeteners with a high intense sweetness that can be combined with the compounds or derivatives of formula (2), inclusive of formula (1), and also inclusive of those derivatices where $R_8$, $R_9$ and $R_{10}$ are hydrogens can magnify the sweetness in at least approximately 10 times compared to the derivative not so combined with the other sweeteners. Examples of such other sweeteners include, but are not limited to, Aspartame, Acesulfame K, Saccharine (including its salt form such as sodium salt), sodium cyclamate, sucralose, disodium glycyrrhizinate, Alitame, Glycyrrhizin, Stevioside (including its derivative) and Thaumatin. Preferably, Aspartame is used to improve the sweetness quality of the aspartyl dipeptide ester derivative.

In a composition containing the aspartyl dipeptide ester derivative and the other sweetener with a high intense sweetness may be used at the same time, in any form of use. For example, they can be used together as a solid—solid, solid-liquid, liquid—liquid or etc. Further, when they are mixed during manufacture thereof, at least one or a part of both may be mixed in the form of solution, and then dried to be in the form of solid.

The improved sweetness quality is influenced by the various sweetener components, the ratio of those components, amount of the composition used, and the existence of other non-sweetner components. Therefore, the preferred ratios to be employed will vary depending on the use and can be tailored to each individual formulation.

"Sweetness ratio" or "ratio of sweetness intensity" is adopted from a comparative index, which refers to the ratio or the proportion of the sweetness intensity, when the plural of the sweetener components are included therein. The ratio can be calculated from the weight ratio of sucrose corresponding to the sweetness intensity of each component.

For example, when preparing a solution having a intensity of sweetness equivalent to that of 10% sucrose, wherein 80% of the 10% of intensity of sweetness is from the sweetener component A and the residual 20% is from the sweetener component B, the sweetness ratio is A:B=8:2. When the sweetening magnification relative to sucrose varies depending on the composition and the concentration of the sweetener component is varied even if it is a same sweetener component (in this case, an exponential curve can be prepared and used for calculation), the objective weight of the sweetener component can be calculated. For example, if the equation for converting sweetness intensity (the exponential curve) component A is $Y=aX^b$, and the equation for converting sweetness intensity (the exponential curve) of component B is $Y=cX^d$, the weight ratio of the components A and B in the ratio A:B=8:2, can be determined using the following calculation, where Y is a concentration equivalent to that of sucrose (PSE %), and X is the sweetener component concentration (g/100 ml):

Weight % of the sweetener component $A=100\times[INV((\ln(8/a))/b)]/[INV((\ln(8/a))/b)+INV((\ln(2/c))/d)]$ If component B is a sweetener with a low intensity sweetness and the sweetness magnification is low: h times constant (there is no sweetness intensity curve), the weight % may be determined as follows:

Weight % of the sweetener component $A=100\times[INV((\ln(8/a))/b)]/[INV((\ln(8/a))/b)+2/h]$ If Aspartame is used in the composition of the present invention, the sweetness quality closer to that of sucrose can be produced by including it in the mixed composition with the aspartyl dipeptide ester derivative, at the ratio of not less than about 5%, preferably about from 5 to 90%, more preferably from about 20 to 90% therein by the ratio of sweetness intensity. As the sweetness intensity varies depending on the derivative, the ranges of the weight ratio can be determined in each case. However, if the weight ratio is applicable to all cases regardless of the derivative, Aspartame can be mixed into the composition in amounts of from 5 to 99.9%, preferably about 10 to 99.9%, and more preferably about 20 to 99.8% by weight to a total amount of one or more the derivatives and Aspartame. Where only one derivative is present, Aspartame can be mixed in an amount of from 60 to 99.8%, preferably approximately 94 to 99.8% by weight.

In the case of derivative 2, Aspartame can be mixed in an amount of approximately 25 to 99.7%, preferably approximately 77 to 99.7% by weight.

With regard to another sweetener with a high intensity sweetness other than Aspartame, the suitable range of composition can be determined accordingly. The preferred ratio can be selected by studying the ratio of sweetness intensity as described above, and can be mixed in an amount of from about 1 to about 99.9% by weight according to the components mixed.

It is generally preferred to use the sweetness intensity equivalent to that of 10% sucrose (which is referred to as "PSE 10%". PSE: abbreviation of Point of Subjective Equality) in beverages, such as a cola drink, and 5% sucrose (PSE 5%) in black teas, coffees and the like.

In addition, different sweeteners and other components other than sweeteners can be added, for example, salt such as sodium chloride, which can improve the quality of sweetness of the aspartyl dipeptide ester derivative.

The compositions of the present invention may also include a carrier, a bulking agent and/or a filler, which are known and used in the art.

For example, carriers include, but are not limited to, a general sugar (sucrose, invert sugar, isomerized sugar, glucose, fructose, lactose, malt sugar, D-xylose and isomerized lactose, etc.), sugar alcohol (maltitol (reduced maltose syrup, etc.), sorbitol, mannitol, erythritol, xylitol, lactitol (reduced lactose, etc.), palatinit, and hydrogenated starch hydrolysate (reduced starch syrup, etc.), etc.), oligosaccharide (fructooligosaccharide (neosuga, etc.), maltooligosaccharide (linear chain oligosaccharide, etc., isomaltooligosaccharide (branched chain oligosaccharide, etc.), galactooligosaccharide, soy been oligosaccharide, lactooligosaccharide, etc.), a derivative of sucrose (sucrose binding starch sugar, etc. (coupling sugar: glucosylsucrose and so on), etc.), palatinose (isomaltulose and so on), trehalose, etc.), polysaccharide (glucomannan, etc.), dietary fiber (enzyme decomposition product of guar gum (hydrolysate of galactomannan, etc.), non-digestible dextrin (dietary fiber containing dextrin, etc.), polydextrose, etc.), and starch (dextrin, soluble starch, modified starch, etc.) can be used. When such carriers are used, a single compound included in these compounds or a mixture of plural compounds therein can be suitably selected and used.

The food and beverage products that are in need of sweet taste, include, but are not limited to, a confectionary (an ice cream or a sherbet, a jelly, a cake, a candy), bread, chewing gum, a sanitary product, cosmetics (including an oral composition such a tooth paste), a chemical (medicine) and an animal product other than human. The sweetener composition of the present invention can be used both in the form of such sweetened products, and also in a method for imparting sweetness to the product, which is in need of sweetness. In this case, objective sweetness can be easily imparted by adding or including said sweetener composition to or in the product such as food and drink and so on which is in need of sweetness or the intermediate product during its manufacture. With regard to the method for using the sweetener composition (for example, the method of adding or including it), any method which is known for using a sweetener component for a sweetener or a method for imparting the sweetness (sweet taste) and so on can be employed.

As disclosed above, sugar, sugar alcohol and oligosaccharide can be used in the present invention (hereafter "sugar and so on used in the present invention").

The sugars used can be any sugar that has a sweet taste and preferably is also soluble in water. For example, sucrose (including derivative thereof), invert sugar, isomerized sugar, glucose, fructose, lactose, malt sugar, D-xylose and isomerized lactose. The derivatives of sucrose are, for example, sucrose binding starch sugar (including coupling sugar, glucosylsucrose, etc.), palatinose (including isomaltulose, etc.) and trehalose, etc.

The term "sugar alcohol" means a reduced sugar, and the term "oligosaccaride" means a polysaccharide that has several basic monosaccharide units, such as glucose and fructose. Sugar alcohols, include, but are not limited to, maltitol, sorbitol, mannitol, erythritol, xylitol, lactitol, palatinit, and reduced starch sugar. Examples of oligosaccharides include fructo-oligosaccharide, maltooligosaccharide, isomaltooligosaccharide, galactooligosaccharide, soy been oligosaccharide and lactooligosaccharide.

These sugar or sugar compounds can be used singly or in combination.

Among the above described sugar compounds, in view of improving the sweetness quality of the aspartyl dipeptide ester derivative(s) used in the present invention, sucrose is preferred. In view of a superior effect, sugar alcohols are preferred, and more preferred are erythritol, maltitol, sorbitol, xylitol, etc.

In the composition of the present invention, at least one aspartyl dipeptide ester derivative and any one of sugar, sugar alcohol and oligosaccharide may be used together, in any form. For example, they can be in the form of two solids, two liquids, one solid and one liquid, etc. Further, when they are mixed during manufacture, at least one or a part of both may be mixed in the form of solution, and then dried to be in the form of solid.

When sucrose is used in the present invention, the ratio of sucrose with the aspartyl dipeptide ester derivative is not less than about 5%, preferably approximately 5 to 95%, more preferably approximately 20 to 90% in a mixture sweetness ratio. As the sweetness intensity of the derivative (s) is large, the ratio used of the derivatives is in parts per million (ppm). For example, when they are used with sucrose, the derivatives are mixed, in an amount of approximately 0.5 ppm to 5000 ppm (by weight), and preferably approximately 1 ppm to 1000 ppm (by weight) to a total amount of said derivative and sucrose.

Particularly, when derivative 1 is mixed with sucrose, derivative 1 is in an amount of approximately 5 ppm to 850 ppm (by weight), and preferably approximately 5 ppm to 200 ppm (by weight) to a total amount of derivative 1 and sucrose. When derivative 2 is used with, for example, sucrose, derivative 2 is in an amount of from approximately 6 ppm to 4000 ppm (by weight), and preferably approximately 6 ppm to 1000 ppm to a total amount of derivative 2 and sucrose.

When sugar alcohol, particularly one of erythritol, maltitol, sorbitol, and xylitol, is used, the composition with a sweetness quality closer to sucrose can be produced by including the sugar alcohol mixed with the aspartyl dipeptide ester derivative, in an amount not less than about 5%, preferably approximately 5 to 95%, more preferably approximately 20 to 90% therein by the sweetness ratio. When the aspartyl dipeptide ester derivative is mixed with sugar alcohol, the derivative is in an amount of from approximately 0.5 ppm to 5000 ppm (by weight), and preferably approximately 1 ppm to 1000 ppm (by weight) to the total amount.

When derivative 1 is mixed with a sugar alcohol, derivative 1 is in an amount of from approximately 1 ppm to 3000 ppm (by weight), and preferably approximately 1 ppm to 100 ppm (by weight) to a total amount thereof. When derivative 2 is mixed with sugar alcohol, the amount of the derivative can be approximately 1 ppm to 1500 ppm (by weight), and preferably approximately 1 ppm to 300 ppm (by weight).

Relative to the total composition, a preferred concentration of the aspartyl dipeptide derivative is from 0.5 ppm to 5000 ppm (by weight).

When the aspartyl dipeptide ester derivative is mixed with at least one of sugar, sugar alcohol and oligosaccharide other than those described above, the high-quality of sweetness closer to that of sucrose can be imparted when the sugar, sugar alcohol and/or oligosaccharide are in an amount of not less than 5%, preferably approximately 5 to 95%, and more preferably approximately 20 to 90% by sweetness intensity to a total amount thereof.

In another embodiment of the present invention, the aspartyl dipeptide ester derivatives can be formulated into taste modifying composition, which can be used to correct the taste of injestible products, such as foods, beverages, and/or medicinal products. The taste modifier may be in any form and can be used together in the form of the mixture of solid—solid (powder, etc.), and liquid—liquid., When manufactured the components of the taste modifier can be be mixed together homogeneously, and then dried to be in the form of solid.

As an example of compounds or components that impart a bitter taste, which can benefit from the present invention, include, but are not limited to, those products containing arginine, valine, leucine, isoleucine, methionine, histidine, omithine, proline, lysine, other amino acids with a bitter taste, a peptide with a bitter taste, quinine, caffeine, calcium ion, other minerals with, a bitter taste, and a bitter taste found in various herbal medicines, etc. Particularly, ingredients with a bitter taste, include, for example, vinpocetine, fursultiamine; and fursultiamine hydrochloride, sefucaneldaroxicete, cefotiam hexetil hydrochloride, lenampicillin hydrochloride, bacampicillin hydrochloride, talampicillin hydrochloride, pivmecillinam hydrochloride, oxeladin tannate, clobutinol hydrochloride, berberine hydrochloride, propantheline bromide, papaverine hydrochloride, ticlopidine hydrochloride, chlorpromazine hydrochloride, and sultamicillin tosylate (as described in, for example, Japanese Patent Kokai Publication JP-A-H4-327529), anhydrous caffeine, diprophylline, diphenhydramine salicylate, chlorpheniramine maleate, pyridoxine hydrochloride, dimenhydrinate, meclizine hydrochloride, methylephedrine hydrochloride, guaiacol potassium sulfonate, guanethidine, chlorhexidine hydrochloride, dihydrocodeine phosphate, ephedrine hydrochloride, spironolactone tegafur, erythromycin stearate, alacepril, sodium valproate, meclofenoxate hydrochloride, chloramphenicol, aminophylline, erythromycin, calcium hopantate, calcium pantothenate, phenobarbital, cimetidine, etilefrine hydrochloride, pirenzepine hydrochloride, butyl scopolamine hydrochloride, dilteazem hydrochloride, enoxacin, piromidate trihydrate, propranolol hydrochloride, flufenamic acid, chlorpromazine, digitonin, promethazine hydrochloride, metoclopramide hydrochloride, ofloxacin, sulpyrine, acetaminophen, aspirin, ibuprofen, benzydamine hydrochloride, alprenolol hydrochloride, bifemelane hydrochloride, lidocaine, diphenhydramine hydrochloride, sodium tolmetin, nortriptyline hydrochloride, and loperamide hydrochloride (as described in for example Jananese Patent Kokai Publication JP-A-4-327526), and, azelastine hydrochloride, bifemelane hydrochloride, quinidine sulfate, s-(+)-(2-chlorophenyl)-3-cyclopropanecarbonyl-8,11-dimethyl-2,3,4,5-tetrahydro-8H-pyrido-[4,3;4,5]thieno[3,2-f][1,2,4]triazoro[4,3-a][1,4]diazepin (as described in for example Japanese Patent Kokai Publication JP-A-4-282312), (+)-(5R,6S)-6-[(R)-1-hydroxyethyl]-3-(3-pyridyl)-7-oxo-4-thia-1-azabicyclo[3,2,0]hepto-2-ene-2-carboxylic acid acetoxymethyl ester, etc. (as described in Japanese Patent Kokai Publication JP-A-4-257457 (refer to JP Patent Kokai Publication JP-A-6-298668)).

When a bitter taste is present in a product, the effect of the present invention is obtained by using one or a plural of the aspartyl dipeptide ester derivative compounds as described above. Depending on the content of the substance of bitter taste, almost all or a part of the bitter taste can be removed, or the bitter taste can be suppressed to some degree (decreased) by the addition of the aspartyl didpeptide ester derivatives thereof. If the content of the substance of bitter taste is too high, the complete removal of bitter taste may be impossible even by adding some amount of the aspartyl dipeptide ester derivative. In this case, the effect of removing a part of bitter taste or suppressing (decreasing) the bitter taste is expressed by mixing an appropriate amount of the derivative. Thus, the use of said derivative for the effect of removing a part of bitter taste or suppressing (decreasing) the bitter taste is part of the present invention.

One or a plurality of the aspartyl dipeptide ester derivatives can be used as a taste modifier in a product, such as a food, beverage, medicine, etc. The ratio of the aspartyl dipeptide ester derivative (one or more than one) included in the finished product to the total amount of the product, varies depending on the kind of the product. The aspartyl dipeptide ester derivative can be used in an amount of approximately 0.2 weight ppm to 10000 weight ppm, and preferably from approximately 1 weight ppm to approximately 5000 weight ppm. When selecting the amount of the ester derivative to be used, the appropriate amount to have the effect of the sweetness magnification should be taken into account. When the concentration of the derivative used is too low, the effect of correcting the bitter taste is not sufficient, and when it is too high, the taste of the product, particularly when it is used for drink, is problematic (in taste) by the excess of sweetness intesity.

For example, when the solution of PSE 10% (PSE: Point of Subjective Equality) is prepared by using derivative A having 50000 times of magnification of sweetness intensity, 10/50000 g (vs. 100 g solution) of derivative A may be used (the content of derivative A in the solution is equivalent to 2 ppm, and that in the form of solid is 200 ppm). On the other hand, when the solution of PSE 5% is prepared by using derivative B having 4000 times of magnification of sweetness intensity, 5/4000 g (vs. 100 g solution) of derivative B may be used (the content of derivative B in the solution is equivalent to 12.5 ppm, and that in the form of solid is 1250 ppm).

The taste modifying composition can be in any form, such as liquid, powder, granule, tablet, another solid state, paste, etc.

When the aspartyl dipeptide ester derivative is used as a taste modifier by adding it to the product such as food, beverage, or a medicine during manufacture, there is no particular restriction with respect to the time and method of addition thereof.

The invention also provides methods for correcting a taste by adding or including said taste modifier to or in a product, such as a food, beverage, and/or a medicine by adding one or more of the taste modifying compositions described herein to the product, either at an intermediate stage of production, at a beginning stage of production, or at a final stage of production.

The following Examples provide an illustration of embodiments of the invention and should not be construed to limit the scope of the invention, which is set forth in the appended claims.

EXAMPLES

Example 1

Measurement of the Magnification of Sweetness Intensity

An aqueous solution was prepared by diluting derivative 2 to be PSE 10% concentration (15.5 mg/1000 ml=10/6500 g/100 ml), assuming that the intensity of sweetness of derivative 2 was 6500 times that of sucrose. Separately, aqueous sucrose solutions having sucrose concentrations of (a)6.94%, (b)8.33%, (c)10%, (d)12%, and (e)14.4% were prepared. The sensory evaluation was performed by determining which sucrose solution was closest to the solution of derivative 2 in the sweetness intensity. The result of calculation of the average of points of 20 panelists was 2.25 point.

The intensity of sweetness of the solution of derivative 2 was 8.75% according to the following equation: (10.0–8.33)×0.25+8.33=8.75. Accordingly, the intense sweetness of derivative 2 was 5600 (=8.75/0.00155) times that of sucrose. According to the same experiment, the intensity of sweetness of derivative 1 was 22600 times that of sucrose. Furthermore, the magnification of sweetness intensity of other derivatives (3 to 9) can be determined by the same method.

And the magnification of sweetness intensity in the cola drink can be also determined by the same method compared to the control solution of cola drink containing 10% sucrose.

The composition of cola drink is as follows.

| | |
|---|---|
| Citric acid (crystalline) | 0.25 g/1000 ml |
| Sodium citrate | 0.10 g/1000 ml |
| 85% Phosphoric acid | 0.3 g/1000 ml |
| Cola base | 2 ml/1000 ml |
| Cola essence | 1 ml/1000 ml |
| Sweetener (sample) | Prescribed amount |

As for the concentration of the references, the sucrose concentrations of previous (a) to (e) were used. In consequence, the magnification of sweetness intensity in the cola drink of derivative 1 was 22600 times, and that of derivative 2 was 4900 times.

Example 2

Taste Characteristics in an Aqueous Solution

The following experiments were performed using the water obtained by ion exchanging and further distilling the water.

An aqueous solution of each of derivatives 1 to 9 having a sweetness level equivalent to that of PSE 10% was prepared, and compared with aqueous 10% sucrose solution with respect to the following 9 items, i.e., "onset of the taste", "round taste", "clear taste", "lingering taste", "peculiar taste", "heavy taste", "bitter taste", "astringent taste" and "irritation". The results were determined as 5 levels (−2 point: very weak, −1 point: a little weak, 0 point: same, +1 point: a little strong, +2 point: very strong) by 8 panelists, and the average points were calculated. The sample solutions of the derivatives equivalent to PSE 10%, were prepared by using the magnification of sweetness intensity measured in Example 1, and the amounts of each derivatives to be used were as follows.

| Sample | Amount equivalent to PSE 10% (mg/1000 ml) |
|---|---|
| Derivative 1 | 4.5 |
| Derivative 2 | 17.9 |
| Derivative 3 | 2.3 |
| Derivative 4 | 2.3 |
| Derivative 5 | 11.9 |
| Derivative 6 | 6.7 |
| Derivative 7 | 9.0 |
| Derivative 8 | 5.5 |
| Derivative 9 | 12.5 |

(Results of the Taste Characteristics)

All of the derivatives were extremely weak in the onset of the taste, very weak in round and clear taste, extremely strong in lingering taste, and very strong in peculiar, heavy, bitter and astringent taste, and irritation.

Next, the total of the absolute value of the deviation from sucrose in each of the evaluation items consisting of the onset of the taste, the round taste, the clear taste, the lingering taste, the peculiar taste, the heavy taste, the bitter taste, the astringent taste and the irritation was divided by 9 (total number of items) to calculate the similarity (which is referred to as "similarity index"). The smaller the similarity index becomes, the better the taste balances, and the closer the taste is to the taste characteristics (quality) of sucrose. The total taste becomes preferable. The similarity indexes of each derivatives are shown as follows.

| Sample | Similarity index |
|---|---|
| Derivative 1 | 1.17 |
| Derivative 2 | 0.63 |
| Derivative 3 | 1.04 |
| Derivative 4 | 0.93 |
| Derivative 5 | 1.38 |
| Derivative 6 | 0.93 |
| Derivative 7 | 0.86 |
| Derivative 8 | 0.77 |
| Derivative 9 | 0.77 |

Example 3

Taste Characteristics in a Cola Drink

The following experiments were performed in the same way as that of Example 2. Instead of aqueous solution, the cola drink of each of derivatives 1 to 9 having a sweetness level equivalent to that of PSE 10% was prepared, and compared with the cola drink containing 10% sucrose. The evaluation method and so on were same as that of Example 2.

When carbon dioxide is blown in the cola drink, the carbonated cola drink is prepared, however, the taste of the cola drink can be compared more easily in that without carbon dioxide. Thus the sensory evaluation of non-carbonated cola drink was performed.

The composition of the cola drink employed was same as that of Example 1.

| Sample | Amount equivalent to PSE 10% (mg/1000 ml) |
|---|---|
| Derivative 1 | 4.5 |
| Derivative 2 | 20.4 |
| Derivative 3 | 2.7 |
| Derivative 4 | 3.4 |
| Derivative 5 | 12.5 |
| Derivative 6 | 7.1 |
| Derivative 7 | 9.4 |
| Derivative 8 | 6.3 |
| Derivative 9 | 13.3 |

(Results of the taste characteristics)

All of the derivatives were extremely weak in the onset of the taste, very weak in round and clear taste, extremely strong in the lingering taste, and very strong in peculiar, heavy, bitter and astringent taste, and irritation.

The similarity indexes were calculated as those of aqueous solutions. The smaller the similarity index becomes, the better the taste balances, and the closer the taste is to the taste characteristics (quality) of sucrose. The total taste becomes preferable. The similarity indexes of each derivatives are shown as follows.

| Sample | Similarity index |
|---|---|
| Derivative 1 | 0.78 |
| Derivative 2 | 0.80 |
| Derivative 3 | 1.11 |
| Derivative 4 | 1.04 |
| Derivative 5 | 1.34 |
| Derivative 6 | 0.81 |

-continued

| Sample | Similarity index |
| --- | --- |
| Derivative 7 | 0.90 |
| Derivative 8 | 1.00 |
| Derivative 9 | 1.00 |

Example 4

Taste Improvement

The mixture with Aspartame of each of derivatives 1 to 9 was prepared and the sensory evaluation of the taste was performed by the same method as described in Example 3.

The sweetener composition having a sweetness level equivalent to that of PSE 10% was mixed with the following sweetness ratio.

| Derivatives 1 to 9:Aspartame |
| --- |
| 8:2 |
| 5:5 |
| 2:8 |

Equations for calculating sweetness intensity in the cola drink (pH 2.8, 20° C.) are as follows, wherein Y denotes the concentration equivalent to that of sucrose (g/100 ml) and X denotes the concentration of the sweetener (g/100 ml), respectively.

| Sample | Calculating equation |
| --- | --- |
| Derivative 1 | $Y = 212300 \times X^{1.29}$ |
| Derivative 2 | $Y = 1890 \times X^{0.847}$ |
| Derivative 6 | $Y = 9520 \times X^{0.947}$ |
| Derivative 8 | $Y = 3940 \times X^{0.812}$ |

In case of derivative 1,
When Y=9.5, X=0.000425 g/100 ml
When Y=8, X=0.00037 g/100 ml
When Y=5, X=0.00026 g/100 ml
When Y=2, X=0.00013 g/100 ml
When Y=1, X=0.000074 g/100 ml
With regard to Aspartame, the values at 20° C., pH2.8 were calculated, that is
When Y=0.5, X=0.00072
When Y=2, X=0.0053
When Y=5, X=0.0202
When Y=8, X=0.0398
When Y=9, X=0.04726

In all cases, as the ratio of Aspartame became larger, the similarity index became smaller compared to the taste of each of the derivatives alone (refer to Example 3) and it was confirmed to be closer to the taste of sucrose.

When the cola drink having a sweetness level equivalent to that of PSE 10% is prepared by mixing derivative 1 and Aspartame, the ratio (%) of Aspartame included in the total amount of the mixture by weight is calculated as follows.

In case of the sweetness ratio of derivative 1:Aspartame= 9.5:0.5, 0.000425 (derivative 1)+0.00072 (Aspartame)= 0.00115 g/100 ml: the percentage content of Aspartame is 62.6% by weight.

In the same way, in case of the sweetness ratio of derivative 1:Aspartame=8:2,
0.00037 (derivative 1)+0.0053 (Aspartame)=0.00567 g/100 ml: the percentage content of Aspartame is 93.5% by weight. In the same way, when the sweetness ratio of derivative 1:Aspartame=2:8, the percentage content of Aspartame is 99.7% by weight.

The same experiments as described above can be performed by a skilled person in the art for calculating those values of each of derivatives 2 to 9 instead of derivative 1, and those values of the another sweeteners with a high intense sweetness other than Aspartame.

Example 5

Taste Improvement with Other Sweeteners

The mixture with each of Acesulfame K, Sodium Saccharine, Alitame, disodium glycyrrhizinate, Stevioside (including its derivative) and Thaumatin of each of derivatives 1 to 9 was prepared and the sensory evaluation for the taste of the mixture was performed by the same method as described in Example 3.

The sweetener composition having a sweetness level equivalent to that of PSE 10% was prepared with the following sweetness ratio.

| Derivatives 1 to 9:Another sweetener with a high intense sweetness |
| --- |
| 5:5 |
| 8:2 |
| 9:1 |

With regard to Acesulfame K, the magnification of sweetness intensity was determined according to the following equation for calculating sweetness intensity.

$$Y = 19.09 X^{0.424}$$

[Y: concentration equivalent to that of sucrose (g/100 ml); X: concentration of Acesulfame K (g/100 ml)]

For the sweetness intensity of the another sweetener with a high intense sweetness, the following magnifications were used.

Saccharine: 190 times, Sodium Saccharine: 190 times, disodium glycyrrhizinate: 100 times, Alitame: 2000 times, Glycyrrhizin: 170 times, Stevioside: 140 times, and Thaumatin: 850 times.

(Results of the Sensory Evaluation)

With respect to the characteristics of the taste, any one of those another sweetener with a high intense sweetness was very strong in bitter, lingering, and peculiar taste, and strong in irritation, astringent and heavy taste. It was also very weak in round and clear taste, and weak in the onset of the taste. However, by mixing these sweetener(s) with each derivatives 1 to 9, it was confirmed that the taste of each of derivatives 1 to 9 was improved and closer to the balanced taste of sucrose.

For example, though the aqueous solution and the cola drink having a sweetness level equivalent to that of PSE 10% in calculation can be prepared, the sensory evaluation thereof shows that the bitter, peculiar taste and so on are felt strongly, and they are different from that of PSE 10% as sweet taste. The total taste is not preferable. On the contrary, when derivative 1 was mixed with Acesulfame K in the sweetness ratio 5:5, for example, the similarity index is 1.00, when the ratio is 8:2, the similarity index is 1.02, and when the ratio is 9:1, the similarity index is 0.86. Thus, all the balance of the taste was improved, wherein the similarity index of Acesulfame K alone is closer without limit to 2.0, and that of sucrose is 0.

Next, with regard to the mixture of each of derivatives 1 to 9 with sodium cyclamate and suclarose, the sensory evaluation was performed as described above. The sweetener compositions having a sweetness level equivalent to that of PSE 10% were prepared in the following sweetness ratio.

| Derivatives 1 to 9:Another sweetener with a high intense sweetness |
| --- |
| 8:2 |
| 5:5 |
| 2:8 |

For the sweetness intensity of the another sweeteners with a high intense sweetness, were used such magnifications as sodium cyclamate: 30 times, and suclarose: 400 times.

(Results of the Sensory Evaluation)

In all cases, as the ratio of said sweetener with a high intense sweetness became larger, the similarity index of any one of derivatives 1 to 9 became smaller compared to the taste of each of the derivatives alone and it was confirmed to be closer to that of sucrose.

Example 6

Sweetener Composition with Derivative 1 and Aspartame

By using the equation for calculating sweetness intensity in the cola drink (refer to Example 4) and the equation for calculating sweetness intensity of Aspartame (refer to the monthly Journal "Food Chemical" August, page 35, 1997), the necessary amounts of those were calculated. In case of Aspartame, the values at 20° C., pH2.8 were used.

| Derivative 1: Aspartame | Concentration of derivative 1 (mg/1000 ml) | Concentration of Aspartame (mg/1000 ml) |
| --- | --- | --- |
| 9.5:0.5 | 4.20 | 7.2 |
| 8:2 | 3.7 | 53 |
| 5:5 | 2.6 | 202 |
| 2:8 | 1.3 | 398 |

With regard to the 9 items of sweetness quality, the cola drinks of each sample having a sweetness level equivalent to that of PSE 10%, were compared with the cola drink of 10% sucrose for the sensory evaluation. The similarity index of each evaluation item was determined by 8 panelists according to Example 3.

(Results of the Sensory Evaluation)

When the ratio of sweetness intensity of derivative 1 was 95%, the early and round tastes are very weak.
The similarity index is 0.76.

When the ratio of sweetness intensity of derivative 1 was 80%, the early and round tastes are very weak and clear taste is weak. The astringent, lingering, bitter and peculiar tastes are strong.
The similarity index is 0.74.

When the ratio of sweetness intensity of derivative 1 was 50%, the onset of the taste is very weak, and the round and clear tastes are weak. The astringent, lingering and bitter tastes are strong.

The similarity index is 0.64.

When the ratio of sweetness intensity of derivative 1 was 20%, the onset of the taste and round tastes are very weak.
The similarity index is 0.48.

As the similarity index of derivative 1 alone is 0.78, the sweet taste of the composition mixed with at least 5% Aspartame by the ratio of sweetness intensity, is found to be improved.

Example 7

Sweetener Composition with Derivative 2 and Aspartame

The same experiment as Example 6 except for derivative 2 instead of derivative 1 in Example 6 was repeated.

With regard to derivative 2, for the equation for calculating sweetness intensity in the cola drink, that determined in Example 4 was used.

| Derivative 2: Aspartame | Concentration of Derivative 2 (mg/1000 ml) | Concentration of Aspartame (mg/1000 ml) |
| --- | --- | --- |
| 9.5:0.5 | 19 | 7.2 |
| 8:2 | 16 | 53 |
| 5:5 | 9.1 | 202 |
| 2:8 | 3.1 | 398 |

(Results of the sensory evaluation)

When the ratio of sweetness intensity of derivative 2 was 95%, the onset of the taste is very weak, and the round and clear tastes are weak. The lingering taste is very strong and the astringent and bitter tastes are strong.
The similarity index is 0.70.

When the ratio of sweetness intensity of derivative 2 was 80%, the early and round tastes are weak, and the astringent, lingering, and bitter tastes are strong.
The similarity index is 0.50.

When the ratio of sweetness intensity of derivative 2 was 50%, the early, round and clear tastes are weak, and the astringent, lingering, bitter and heavy tastes are strong.
The similarity index is 0.60.

When the ratio of sweetness intensity of derivative 2 was 20%, the onset of the taste is very weak, and the round and clear tastes are weak. The lingering taste is very strong, and the astringent and bitter tastes are strong.
The similarity index is 0.63.

As the similarity index of derivative 2 alone is 0.80, the sweet taste of the composition mixed with at least 5% Aspartame by sweetness intensity is found to be improved.

Example 8

Sweetener Composition with Derivative 2 and Acesulfame K

The same experiment as Example 7 except for Acesulfame K instead of Aspartame in Example 7 was repeated.

With regard to Acesulfame K, as the equation for calculating sweetness intensity in the cola drink, that determined in Example 5 was used.

| Derivative 2:<br>Acesulfame K | Concentration of<br>Derivative 2<br>(mg/1000 ml) | Concentration of<br>Acesulfame K<br>(mg/1000 ml) |
|---|---|---|
| 9.5:0.5 | 4.2 | 1.9 |
| 9:1 | 4.1 | 9.5 |
| 8:2 | 3.7 | 48.9 |
| 5:5 | 2.6 | 424.4 |

(Results of the sensory evaluation)

When the ratio of sweetness intensity of derivative 2 was 95%, the onset of the taste and round tastes are weak. The astringent, lingering, bitter and peculiar tastes are strong.
The similarity index is 0.63.

When the ratio of sweetness intensity of derivative 2 was 90%, the onset of the taste, round and clear tastes are weak, and the bitter taste, irritation, astringent, lingering, peculiar and heavy tastes are strong.
The similarity index is 0.76.

When the ratio of sweetness intensity of derivative 2 was 80%, the round taste is very weak, and the onset of the taste and clear tastes are weak. The bitter taste is very weak, and the irritation, astringent, peculiar and lingering tastes are strong.
The similarity index is 0.77.

When the ratio of sweetness intensity of derivative 2 was 50%, the onset of the taste, round and clear tastes are weak. The astringent taste is very strong, and the irritation, astringent, peculiar, lingering and heavy tastes are strong.
The similarity index is 0.90.

As the similarity index of derivative 2 alone is 0.80, the sweet taste of the composition mixed with at most 20% Acesulfame K by the ratio of sweetness intensity is found to be improved.

Example 9

Taste Improvement by Salt

To the aqueous solution of derivative 1 having a sweetness level equivalent to that of PSE 10%, salt was added as final concentratins of 0.1%, 0.2% and 0.5% to compare with the aqueous solution of 10% sucrose for by 2 points comparison method (n=8) and evaluate the characteristics of the taste.

The equation for calculating sweetness intensity of derivative 1 in the aqueous solution is as follows.

$$Y=6980X^{0.848}$$

| Sample<br>No. | Concentration of<br>derivative 1 (mg/100 ml) | NaCl addition (%) | PSE (%) |
|---|---|---|---|
| 1 | 0.46 | 0.1 | 10 |
| 2 | 0.46 | 0.2 | 10 |
| 3 | 0.46 | 0.5 | 10.4 |

The sensory evaluation was performed by the same way as Example 6.
(Results of the Sensory Evaluation)

When salt was added in 0.1%, the onset of the taste, round and clear tastes are weak. The lingering, bitter, irritation, heavy and peculiar tastes are strong.
The similarity index is 0.77.

When salt was added in 0.2%, the onset of the taste and clear tastes are weak. The lingering, and peculiar tastes are very strong. The irritation and heavy taste are strong.

The similarity index is 0.79.

When salt was added in 0.5%, the onset of the taste, and clear tastes are weak. The lingering and peculiar tastes, and irritation are very strong. The heavy taste is strong.

The similarity index is 0.83.

As the similarity index of derivative 1 in the aqueous solution is 1.17 (refer to Example 2), the sweet taste of the composition by addition of salt is found to be improved. Other derivatives (derivatives 2 to 9) were evaluated by the same method as described above, and it was found that the addition of salt was effective and the amount of addition of salt not more than 0.3% by weight was preferable for improving the taste.

Example 10

Use in a Carbonated Cola Drink

The carbonated cola drink was produced in the following composition.

| Component | Product of the<br>present<br>invention[1] | Reference product<br>1[2] | Reference<br>product 2 |
|---|---|---|---|
| Sucrose | | | 100 g |
| Derivative 2 | 9.1 mg | 20.5 mg | |
| Aspartame | 202 mg | | |
| Citric acid<br>(crystal) | 0.25 g | 0.25 g | 0.25 g |
| Sodium citrate | 0.10 g | 0.10 g | 0.10 g |
| 85% Phosphoric<br>acid | 0.3 g | 0.3 g | 0.3 g |
| Cola base | 2 ml | 2 ml | 2 ml |
| Cola essence | 1 ml | 1 ml | 1 ml |
| Distilled water | to 1000 ml[3] | to 1000 ml[3] | to 1000 ml[3] |

[1]Sweetness ratio 5:5, PSE 10%, pH 2.8
[2]PSE 10% with derivative 2 alone, pH 2.8
[3]Addition of distilled water to final volume 1000 ml.

1000 ml of each of the above-obtained cola drinks (the product of the present invention, the reference product 1 or the reference product 2) was charged into a carbonation gas cylinder, and carbon dioxide gas was charged therein. The gas cylinder was stored in the refrigerator for overnight. When it was cooled well, the bomb was opened while it stood still, and the solution thereof was immediately charged into 240 ml can.

(Evaluation of the Sweetness Quality)

With respect to the products (PSE 10%) obtained by the method as described above, the sensory evaluation was performed by the same way. As a result, with respect to the reference product 1, the onset of the taste was very weak, the lingering taste was very strong, and the astringent taste was strong. On the contrary, with respect to the product of the present invention, the sweetness quality was improved such that the onset of the taste became stronger and the lingering and astringent tastes became weaker, the well-balanced taste characteristics were shown and also the total taste became preferable (n=20).

Example 11

Production of Sweetener for Tabletop Use

The sweetener was produced by mixing well the following components.

| Component | Weight (g) | Composition (weight %) |
|---|---|---|
| Derivative 2 | 0.66 | 0.10 |
| Aspartame | 1.38 | 0.21 |
| Erythritol | 666.67 | 99.40 |
| Flavor | 1.97 | 0.29 |
| Total amount | 670.68 | 100 |

When 0.94 g of the sweetener produced (sample) were added to 140 ml (volume for the standard coffee cup) of coffee solution, the sweetness intensity of said coffee solution is equivalent to that of PSE 5%. The sweetness ratio of the sweetener is in derivative 2:Aspartame:Erythritol= 4:0.5:0.5, and herein the magnification of sweetness intensity of the derivative 2 at PSE 4% was calculated as 6000 times, the magnification of sweetness intensity of Aspartame at PSE 0.5% was calculated as 360 times and the magnification of sweetness intensity of Erythritol even at PSE 0.5% was calculated as 0.75 times.

0.94 g (/one cup[140 ml]) of the above sweetener for tabletop use was added to coffee as a sweetener, and thus obtained coffee was compared to the coffee with 5 g of sucrose (/one cup[140 ml]) added by the sensory evaluation. There was no significant difference between the sweet tastes of the both, and the coffee using the above sweetener for tabletop use showed a similar sweetness (sweet taste) to that of sucrose with totally preferable taste (n=20). And the above tabletop sweetener is superior in that the calorie of the sweetener is close to zero.

Example 12

Production of a Sherbet (Ice Block; Block Ice)

A sherbet (a block ice) is produced usually by freezing the aqueous solution of sucrose and flavors. Herein the sweetness of sucrose was replaced by that of the derivative used in the present invention. As the depression of freezing point of the derivative used in the present invention is smaller than that of sucrose, the freezing point thereof rose by 4 to 5° C. Therefore, it froze easily, it is difficult to prepare unevenness on freezing, and the surface thereof did not weep ("Naki"in Japanese was not found). Further, it had a good long time stability for storage. When a fruit flavor was used, the product of good fruit juice flavor was obtained. Example: block ice (coffee type)

| Component | Composition (weight %) |
|---|---|
| Extract of coffee (Brix44.1) | 0.9 |
| Derivative 1 | 0.0002 |
| Aspartame | 0.038 |
| Deionized water | 99.0618 |
| Total amount | 100 |

PH 4.9; Bx.44.1

The sweetness ratio of said block ice is derivative 1:Aspartame=5:5, wherein the magnification of the sweetness intensity of derivative 1 at PSE 5% was calculated as 25600 times, and that of Aspartame at PSE 5% was calculated as 130 times.

Example 13

Production of an Orangeade

The orangeades were produced in the following compositions.

| Component | Product of the present invention[1] | Reference product[2] |
|---|---|---|
| Concentrated orange juice[3] | 17.5 g | 17.5 g |
| Liquid sugar of fructose and glucose (Intense sweetness 1) | 18.0 g | 18.0 g |
| PO-40[4] | 27.7 g | 27.7 g |
| Derivative 4 | 0.00012 g | 0.00015 g |
| Aspartame | 0.0506 g | — |
| Citric acid | 3 g | 3 g |
| Vitamin C | 0.2 g | 0.2 g |
| Distilled water | To 1000 g | to 1000 g |

[1]Total sweetness ratio of sweetness intensity of total product; derivative 4:Aspartame:sweetness derived from concentrated fruit juice:sweetness derived from the liquid sugar of fructose and glucose:sweetness derived from PO-40 = 5.1:1.2:1.1:1.8:0.8.
The sweetness ratio between two types of the sweetener with a high intense sweetness; derivative 4:Aspartame = 8:2.
[2]Total sweetness ratio; derivative 4:sweetness derived from concentrated fruit juice:sweetness derived from liquid sugar of fructose and glucose:sweetness derived from PO-40 = 6.3:1.1:1.8:0.8.
[3]IRF 1/5.7 (intensity of sugar 63.6)
[4]Towa Kasei Co. Ltd., Reduced starch sugar, solid matter 70% (intensity of sweetness 0.4).

Both products of the present invention and the reference for the above orangeade contain 10% fruit juice, 10% intensity of sweetness (PSE), 16.5 Kcal total energy (they can be labeled as "low-calorie" because it is not more than 20 Kcal which is a standard of showing nutrition therefor), and 2.46 g/100 g sugar (they can be labeled as "low-sugar" because it is not more than 2.5 g/100 g which is a standard of showing nutrition therefor).

Where, the calculation of the sweetness was made by using the equation for calculating sweetness intensity of derivative 4 $Y=58775X^{1.04}$. When $Y=6.3\%$, $X=0.00015$ g/100 ml, When $Y=5.1\%$, $X=0.00012$ g/100 ml.
(Evaluation of the Sweetness Quality)

As described above, the sensory evaluation for the products obtained (PSE 10%) was performed. As a result, the sweetness quality of the product of the present invention was improved in comparison with that of the reference product such that the onset of the taste became stronger, the astringent and bitter tastes became weaker, and the well-balanced taste characteristics was shown and the total taste was preferable (n=20).
(Second Invention of the Present Invention)

Example 14

Magnification of Sweetness Intensity

An aqueous solution was prepared by diluting derivative 2 to be PSE 10% concentration (15.5 mg/1000 ml=10/6500 g/100 ml), assuming that the intensity of sweetness of derivative 2 was 6500 times that of sucrose. Separately, aqueous sucrose solutions having sucrose concentrations of (a)6.94%, (b)8.33%, (c)10%, (d)12%, and (e)14.4% were prepared. The sensory evaluation was performed by determining which sucrose solution was closest to the solution of derivative 2 in the sweetness intensity. The result of calculation of the average of points of 20 panelists was 2.25 point.

The intensity of sweetness of the solution of derivative 2 was 8.75% according to the following equation: (10.0−8.33)×0.25+8.33=8.75. Accordingly, the intensity of sweetness of derivative 2 was 5600 (=8.75/0.00155) times that of sucrose. According to the same experiment, the intensity of sweetness of derivative 1 was 22600 times that of sucrose. Furthermore, the magnification of sweetness intensity of other derivatives (3 to 9) can be determined by the same method.

And the magnification of sweetness intensity in the cola drink can be also determined by the same method compared to the reference solution of cola drink containing 10% sucrose.

The components of cola drink is as follows.

| | |
|---|---|
| Citric acid (crystal) | 0.25 g/1000 ml |
| Sodium citrate | 0.10 g/1000 ml |
| 85% Phosphoric acid | 0.3 g/1000 ml |
| Cola base | 2 ml/1000 ml |
| Cola essence | 1 ml/1000 ml |
| Sweetener (sample) | Prescribed amount |

As for the concentration of the references, the sucrose concentrations of previous (a) to (e) were used. As the results, the magnification of sweetness intensity in the cola drink of derivative 1 was 22600 times, and that of derivative 2 was 4900 times.

Example 15

Taste Characteristics in an Aqueous Solution

The following experiments were conducted using the water obtained by ion exchanging and further distilling tap water.

An aqueous solution of each of derivatives 1 to 9 having a sweetness level equivalent to that of PES 10% was prepared, and compared with aqueous 10% sucrose solution with respect to 9 items, namely, "the onset of the taste", "round taste", "clear taste", "lingering taste", "peculiar taste", "heavy taste", "bitter taste", "astringent taste" and "irritation". The results were determined as 5 levels (−2 point: very weak, −1 point: a little weak, 0 point: same, +1 point: a little strong, +2 point: very strong) by 8 panelists, and the average points were calculated. Results were as follows.

| Sample | Amount equivalent to PSE 10% (mg/1000 ml) |
|---|---|
| Derivative 1 | 4.5 |
| Derivative 2 | 17.9 |
| Derivative 3 | 2.3 |
| Derivative 4 | 2.3 |
| Derivative 5 | 11.9 |
| Derivative 6 | 6.7 |
| Derivative 7 | 9.0 |
| Derivative 8 | 5.5 |
| Derivative 9 | 12.5 |

(Results of the taste characteristics)

All of the derivatives were extremely weak in the onset of the taste, very weak in round and clear taste, extremely strong in lingering taste, and very strong in peculiar, heavy, bitter and astringent taste, and irritation.

Next, the total of the absolute value of the deviation from sucrose in each of the evaluation items consisting of onset of the taste, round taste, clear taste, lingering taste, peculiar taste, heavy taste, bitter taste, astringent taste and irritation was divided by 9 (total number of items) to calculate the similarity (which is refer to as "similarity index"). The smaller the similarity index becomes, the better the taste balances, and the closer the taste is to the taste characteristics (quality) of sucrose. The total taste becomes preferable. The similarity indexes of each of the derivatives are shown as follows.

| Sample | Similarity index |
|---|---|
| Derivative 1 | 1.17 |
| Derivative 2 | 0.63 |
| Derivative 3 | 1.04 |
| Derivative 4 | 0.93 |
| Derivative 5 | 1.38 |
| Derivative 6 | 0.93 |
| Derivative 7 | 0.86 |
| Derivative 8 | 0.77 |
| Derivative 9 | 0.77 |

Example 16

Taste Characteristics in a Cola Drink

The following experiments were conducted in the same way as that of Example 15. Instead of aqueous solution, the cola drink of each of derivatives 1 to 9 having a sweetness level equivalent to that of PSE 10% was prepared, and compared with the cola drink containing 10% sucrose. All of the evaluation method and so on were same as those of Example 15.

When carbon dioxide is blown in the cola drink, the carbonated cola drink is prepared, however, the taste of the cola drink can be compared more easily in that without carbon dioxide. Thus the non-carbonated cola drink was organoleptically evaluated.

The composition of the cola drink employed was same as that of Example 14.

| Sample | Amount equivalent to PSE 10% (mg/1000 ml) |
|---|---|
| Derivative 1 | 4.5 |
| Derivative 2 | 20.4 |
| Derivative 3 | 2.7 |
| Derivative 4 | 3.4 |
| Derivative 5 | 12.5 |
| Derivative 6 | 7.1 |
| Derivative 7 | 9.4 |
| Derivative 8 | 6.3 |
| Derivative 9 | 13.3 |

(Results of the taste characteristics)

All of the derivatives were extremely weak in the onset of the taste, very weak in round and clear taste, extremely strong in lingering taste, and very strong in peculiar, heavy, bitter and astringent taste, and irritation.

The similarity indexes were calculated as those of aqueous solutions. The smaller the similarity index becomes, the better the taste balances, and the closer the taste is to the taste characteristics (quality) of sucrose. The total taste becomes preferable. The similarity indexes of each of the derivatives are shown as follows.

| Sample | Similarity index |
| --- | --- |
| Derivative 1 | 0.78 |
| Derivative 2 | 0.80 |
| Derivative 3 | 1.11 |
| Derivative 4 | 1.04 |
| Derivative 5 | 1.34 |
| Derivative 6 | 0.81 |
| Derivative 7 | 0.90 |
| Derivative 8 | 1.00 |
| Derivative 9 | 1.00 |

Example 17

Taste Improvement by Sugar and Others

The mixture of each sample of derivatives 1 to 9 with sugar and so on used in the present invention was prepared and the sensory evaluation was performed by comparing with the cola drink containing 10% sucrose concentration in the same manner as the method described in Example 16.

The sweetener composition with the sugar and so on equivalent to the sweetness level of PSE 10% was prepared in the following sweetness ratio.

| Derivatives 1 to 9:Sugar and so on |
| --- |
| 8:2 |
| 5:5 |
| 2:8 |

Examples for equations for calculating sweetness intensity in the cola drink (pH2.8, 20° C.) are as follows, and another equations can be prepared in the same manner, wherein Y denotes the concentration equivalent to that of sucrose (g/100 ml) and X denotes the concentration of the sweetener (g/100 ml), respectively.

| Sample | Equations for calculating sweetness intensity |
| --- | --- |
| Derivative 1 | $Y = 212300 \times X^{1.29}$ |
| Derivative 2 | $Y = 1890 \times X^{0.847}$ |
| Derivative 6 | $Y = 9520 \times X^{0.947}$ |
| Derivative 8 | $Y = 3940 \times X^{0.812}$ |

As the sugar and so on used in the above present invention, at least one of the following compounds can be used, and the following numerical values put in the brackets were used as the magnification of sweetness intensity of those compounds.

Sugar: Sucrose (1), invert sugar (1), isomerized sugar (1), glucose (0.6), fructose (1.4), lactose (0.2), malt sugar (0.3), D-xylose (0.4) and isomerized lactose (0.6).

Sugar alcohol: maltitol (reduced maltose syrup) (0.75), sorbitol (0.75), mannitol (0.6), erythritol (0.75), xylitol (1), lactitol (reduced lactose) (0.35), paratinit (0.45), and reduced starch sugar (hydrogenated starch syrup) (0.5).

Oligosaccharide: fructooligosaccharide (neosugar) (0.5), maltooligosaccharide (linear chain oligosaccharide) (0.33), isomaltooligosaccharide (branched chain oligosaccharide) (0.5), galactooligosaccharide (0.2), soy been oligosaccharide (0.7) and lactooligosaccharide (0.8).

A derivative of sucrose: sucrose binding starch sugar (coupling sugar: glucosylsucrose) (0.5), paratinose (isomaltulose) (0.4) and trehalose (0.45).

(Results of the Sensory Evaluation)

In all cases, as the ratio of sweetness intensity of the sugar and so on used in the present invention became larger, the similarity index became smaller compared to the result of each of derivatives 1 to 9 alone (refer to Example 16) and it was confirmed that the taste becomes closer to that of sucrose.

In addition, the another sugar and so on which is not exemplified above (sugar and so on used in the present invention) may show the same effect by doing the same experiment, if preformed.

Example 18

Sweetener Composition of Derivative 1 and Sucrose

With respect to the sweetener compositions of derivative 1 and sucrose the sensory evaluation was performed by comparing with the cola drink with sucrose dissolved therein in a 10% concentration according to the method described in Example 16.

Those sweetener compositions equivalent to the sweetness level of PSE 10% were prepared in the following sweetness ratio. The amount necessary for derivative 1 was calculated by using the equation for calculating sweetness intensity in the cola drink (refer to Example 17).

| Derivative 1:Sucrose (Sweetness ratio) | Concentration of derivative 1 (mg/1000 ml) | Concentration of Sucrose (mg/1000 ml) |
| --- | --- | --- |
| 9.5:0.5 | 4.3 | 5 |
| 8:2 | 3.7 | 20 |
| 5:5 | 2.6 | 50 |
| 2:8 | 1.3 | 80 |
| 0.5:9.5 | 0.4 | 95 |

With regard to the 9 items of sweetness quality described above, the cola drinks with each sample having a sweetness level equivalent to that of PSE 10%, were compared with the cola drinks with 10% sucrose for the sensory evaluation. The similarity index of each item of evaluation was determined by 8 panelists according to Example 16.

(Results of the Sensory Evaluation)

The similarity index of derivative 1 alone is 0.78, and however, by mixing therewith sucrose, the sweet tastes of the compositions thus obtained such as the onset of the taste and lingering taste were improved, and the effect of the improvement became much more as the sweetness ratio of sucrose became larger.

| Derivative 1:Sucrose (Sweetness ratio) | Similarity index |
| --- | --- |
| 9.5:0.5 | 0.75 |
| 8:2 | 0.73 |
| 5:5 | 0.66 |
| 2:8 | 0.51 |
| 0.5:9.5 | 0.35 |

Next, the relationship between the sweetness ratio and the weight ratio of derivative 1 and sucrose and so on are shown.

It can be calculated by using the equation for calculating sweetness intensity on the derivative 1 (refer to Example 17).

When the sweetness ratio is derivative 1 sucrose, lactose and so on=0.5:9.5,
derivative 1 of PSE 0.5%:0.0000434 g/dl;
sucrose and so on of PSE 9.5% (intensity of sweetness 1):9.5 g/dl; and
lactose and so on of PSE 9.5% (intensity of sweetness 0.2):9.5/0.2 g/dl.

Therefore, the weight % of derivative 1 in the mixture is in the following:
(a) In case of mixture with sucrose and so on (intensity of sweetness 1), 4.6 ppm=100×(0.0000434 g/dl)/(0.0000434 g/dl+9.5 g/dl).
(b) In case of mixture with lactose and so on (intensity of sweetness 0.2), 0.9 ppm=100×(0.0000434 g/dl)/(0.0000434 g/dl+47.5 g/dl)

When the sweetness ratio is derivative 1:sucrose, lactose and so on=2:8,
  in case of mixture with sucrose and so on (intensity of sweetness 1);the ratio (weight, ppm) of derivative 1 in the mixture is as follows.

| Derivative 1:Sucrose and so on (Sweetness ratio) | Ratio of derivative 1 by weight in the mixture (ppm) |
| --- | --- |
| 2:8 | 16 |
| 8:2 | 185 |
| 9.5:0.5 | 849 |

Therefore, it is understood that they may be mixed suitably in the range of the weight ratio (ppm) of derivative 1 in the mixture of from 0.9 ppm considering the case of low intense sweetness such as that of lactose and so on (intensity of sweetness 0.2), to 849 ppm in case of 95% of the sweetness intensity when mixing with sucrose and so on (intensity of sweetness 1), and preferably, from 1 to 900 ppm.

Next, the relationship between the sweetness ratio and the weight ratio of derivative 2 and sucrose and so on are shown.

It can be calculated by using the equation for calculating sweetness intensity on the derivative 2 (refer to Example 17).

When the sweetness ratio is derivative 2:sucrose, lactose and so on=0.5:9.5,
Derivative 2 of PSE 0.5% 1:0.0000597 g/dl;
sucrose and so on of PSE 9.5% (intensity of sweetness 1):9.5 g/dl; and
lactose and so on of PSE 9.5% (intensity of sweetness 0.2):9.5/0.2 g/dl.

The weight ratio of derivative 2 in the mixture with lactose and so on (intensity of sweetness 0.2) mixtured was 1.26 ppm.

When the sweetness ratio is derivative 2:sucrose, lactose and so on=9.5:0.5,
  the weight ratio of derivative 2 in the mixture with sucrose and so on (intensity of sweetness 1) mixed was 3850 ppm.

Therefore, it is understood that they may be mixed in the range of the weight ratio of derivative 2 in the mixture of from 1.26 to 3850 ppm, and preferably, from 1 to 4000 ppm, as determined above.

When they are thus calculated for all of the derivatives used in the present invention, the weight ratio (value) applicable to all the derivatives for the present invention is in the range of 0.5 to 5000 ppm.

Example 19

Sweetener Composition with Derivative 2 and Sucrose

With respect to the sweetener compositions of derivative 2 and sucrose the sensory evaluation was performed by comparing with the cola drink with sucrose dissolved therein in a 10% concentration according to the method described in Example 16.

Those sweetener compositions equivalent to the sweetness level of PSE 10% were prepared in the following sweetness ratio. The amount necessary for derivative 2 was calculated by using the equation for calculating sweetness intensity in the cola drink (refer to Example 17).

| Derivative 2:Sucrose (Sweetness ratio) | Concentration of derivative 2 (mg/1000 ml) | Concentration of Sucrose (mg/1000 ml) |
| --- | --- | --- |
| 9.5:0.5 | 19.3 | 5 |
| 8:2 | 15.8 | 20 |
| 5:5 | 9.1 | 50 |
| 2:8 | 3.1 | 80 |
| 0.5:9.5 | 0.5 | 95 |

With regard to the 9 items of sweetness quality described above, the cola drinks with each sample having a sweetness level equivalent to that of PSE 10%, were compared with the cola drinks with 10% sucrose for the sensory evaluation. The similarity index for each item of evaluation was determined by 8 panelists according to Example 16.

(Results of the Sensory Evaluation)

The similarity index of derivative 2 alone is 0.80, and however, by mixing therewith sucrose, the sweet taste of the compositions thus obtained such as the onset of the taste and lingering taste were improved, and the effect of the improvement became much more as the sweetness ratio of sucrose became larger.

| Derivative 2:Sucrose (Sweetness ratio) | Similarity index |
| --- | --- |
| 9.5:0.5 | 0.75 |
| 8:2 | 0.42 |
| 5:5 | 0.46 |
| 2:8 | 0.31 |
| 0.5:9.5 | 0.20 |

Example 20

Sweetener Composition with Derivative 1 and Erythritole

With respect to the sweetener compositions of derivative 1 and erythritol the sensory evaluation was performed by comparing with the cola drink with sucrose dissolved therein in a 10% concentration according to the method described in Example 16.

Those sweetener compositions equivalent to the sweetness level of PSE 10% were prepared in the following sweetness ratio. The amounts necessary for derivative 1 were calculated by using the equation for calculating sweetness intensity in the cola drink (refer to Example 17).

| Derivative 1:Erythritol (Sweetness ratio) | Concentration of derivative 1 (mg/1000 ml) | Concentration of Erythritol (mg/1000 ml) |
| --- | --- | --- |
| 9.5:0.5 | 4.3 | 6.7 |
| 8:2 | 3.7 | 26.7 |
| 5:5 | 2.6 | 66.7 |

-continued

| Derivative 1:Erythritol (Sweetness ratio) | Concentration of derivative 1 (mg/1000 ml) | Concentration of Erythritol (mg/1000 ml) |
|---|---|---|
| 2:8 | 1.3 | 106.7 |
| 0.5:9.5 | 0.4 | 126.7 |

With regard to the 9 items of sweetness quality described above, the cola drinks with each sample having a sweetness level equivalent to that of PSE 10%, were compared with the cola drinks with 10% sucrose for the sensory evaluation. The similarity index for each item of evaluation was determined by 8 panelists according to Example 16.

(Results of the Sensory Evaluation)

The similarity index of derivative 1 alone is 0.78, and however, by mixing therewith erythritol, the sweet taste of the compositions thus obtained such as the onset of the taste, lingering and bitter tastes were improved, and the effect of the improvement became much more as the sweetness ratio of erythritol became larger.

| Derivative 1:Erythritol (Sweetness ratio) | Similarity index |
|---|---|
| 9.5:0.5 | 0.75 |
| 8:2 | 0.74 |
| 5:5 | 0.72 |
| 2:8 | 0.35 |
| 0.5:9.5 | 0.30 |

Example 21

Sweetener Composition with Derivative 2 and Erythritol

With respect to the sweetener compositions of derivative 2 and erythritol the sensory evaluation was performed by comparing with the cola drink with sucrose dissolved therein in a 10% concentration according to the method described in Example 16.

Those sweetener compositions equivalent to the sweetness level of PSE 10% were prepared in the following sweetness ratio. The amounts necessary for derivative 2 were calculated by using the equation for calculating sweetness intensity in the cola drink (refer to Example 17).

| Derivative 2:Erythritol (Sweetness ratio) | Concentration of derivative 2 (mg/1000 ml) | Concentartion of Erythritol (mg/1000 ml) |
|---|---|---|
| 9.5:0.5 | 19.3 | 6.7 |
| 8:2 | 15.8 | 26.7 |
| 5:5 | 9.1 | 66.7 |
| 2:8 | 3.1 | 106.7 |
| 0.5:9.5 | 0.5 | 126.7 |

With regard to the 9 items of sweetness quality described above, the cola drinks with each sample having a sweetness level equivalent to that of PSE 10%, were compared with the cola drinks with 10% sucrose for the sensory evaluation. The similarity index for each item of evaluation was determined by 8 panelists according to Example 16.

(Results of the Sensory Evaluation)

The similarity index of derivative 2 alone is 0.80, and however, by mixing therewith erythritol, the sweet taste of the compositions thus obtained such as the onset of the taste and lingering taste were improved, and the effect of the improvement became much more as the sweetness ratio of erythritol became larger.

| Derivative 2:Erythritol (Sweetness ratio) | Similarity index |
|---|---|
| 9.5:0.5 | 0.65 |
| 8:2 | 0.60 |
| 5:5 | 0.46 |
| 2:8 | 0.30 |
| 0.5:9.5 | 0.25 |

Example 22

Use for a Carbonated Cola (No.1)

The carbonated cola drinks were produced in the following compositions.

| Component | Product of the present invention[*1] | Reference product 1[*2] | Reference product 2 |
|---|---|---|---|
| Derivative 1 | 2.6 mg | 4.4 mg | |
| Sucrose | 50 g | | 100 g |
| Citric acid (crystaline) | 0.25 g | 0.25 g | 0.25 g |
| Sodium citrate | 0.10 g | 0.10 g | 0.10 g |
| 85% Phosphoric acid | 0.3 g | 0.3 g | 0.3 g |
| Cola base | 2 ml | 2 ml | 2 ml |
| Cola essence | 1 ml | 1 ml | 1 ml |
| Distilled water | to 1000 ml[*3] | to 1000 ml[*3] | to 1000 ml[*3] |

[*1]Sweetness ratio 5:5 (derivative 1:sucrose), PSE 10%, pH 2.8;
[*2]PSE 10% with derivative 1 alone,, pH 2.8;
[*3]Addition of distilled water to final volume 1000 ml.

1000 ml of each of the above-obtained cola drinks (the product of the present invention, the reference product 1 or the reference product 2) was charged into a carbonation bomb, and carbon dioxide gas was charged therein. The bomb was stored in the refrigerator for overnight. When it was cooled well, the bomb was opened while it stood still, and the solution thereof was immediately charged into 240 ml can.

(Evaluation of Sweetness Quality)

With respect to the three products obtained above (PSE 10%), the sensory evaluation in terms of the 9 items described above (the onset of the taste, the peculiar taste, the heavy taste, the irritation, the bitter taste, the lingering taste, a stringent taste, the clear taste and the round taste) was performed in the same way. As a result, the reference product 1 (use of derivative 2 alone) was very weak in the onset of the taste, very strong in the lingering taste, and strong in the astringent taste. On the contrary, the product of the present invention was improved in the sweetness quality such that the onset of the taste became stronger and the lingering and astringent tastes became weaker, and thereby the well-balanced taste characteristics was shown and the total taste thereof was preferable (n=20).

Example 23

Use for a Carbonated Cola (No.2)

The carbonated cola drinks were produced in the following compositions.

| Component | Product of the Present invention*¹ | Reference product 1*² | Reference product 2 |
|---|---|---|---|
| Derivative 2 | 15.8 mg | 20.5 mg | |
| Sucrose | | | 100 g |
| Erythritol | 26.7 mg | | |
| Citric acid (crystaline) | 0.25 g | 0.25 g | 0.25 g |
| Sodium citrate | 0.10 g | 0.10 g | 0.10 g |
| 85% Phosphoric acid | 0.3 g | 0.3 g | 0.3 g |
| Cola base | 2 ml | 2 ml | 2 ml |
| Cola essence | 1 ml | 1 ml | 1 ml |
| Distilled water | to 1000 ml*³ | to 1000 ml*³ | to 1000 ml*³ |

*¹Sweetness ratio 8:2 (derivative 1:Erythritol), PSE 10%, pH 2.8;
*²PSE 10% with derivative 2 alone, pH 2.8;
*³Addition of distilled water to final volume 1000 ml.

1000 ml of each of the above-obtained cola drinks (the product of the present invention, the reference product 1 or the reference product 2) was charged into a carbonation bomb, and carbon dioxide gas was charged therein. The bomb was stored in the refrigerator for overnight. When it was cooled well, the bomb was opened while it stood still, and the solution thereof was immediately charged into 240 ml can.

(Evaluation of Sweetness Quality)

With respect to the three products obtained above (PSE 10%), the sensory evaluation in terms of the 9 items described above, was performed in the same way. As a result, the reference product 1 (use of derivative 2 alone) was very weak in the onset of the taste, very strong in the lingering taste, and strong in the astringent taste. On the contrary, the product of the present invention was improved in the sweetness quality such that the onset of the taste became stronger, and the lingering and astringent tastes became weaker, and thereby the well-balanced taste characteristics were shown and the total taste thereof was preferable (n=20).

Example 24

Use for a Carbonated Cola (No.3)

The carbonated cola drinks were produced in the following compositions.

| Component | Product of the present invention*¹ | Reference product 1*² | Reference product 2*³ | Reference product |
|---|---|---|---|---|
| Derivative 1 | 2.2 mg | 4.4 mg | | |
| Derivative 2 | 7.0 mg | | 20.5 mg | |
| Sucrose | 10 g | | | |
| Erythritol | 13.3 g | | | 100 g |
| Citric acid (crystaline) | 0.25 g | 0.25 g | 0.25 g | 0.25 g |
| Sodium citrate | 0.10 g | 0.10 g | 0.10 g | 0.10 g |
| 85% Phosphoric acid | 0.3 g | 0.3 g | 0.3 g | 0.3 g |
| Cola base | 2 ml | 2 ml | 2 ml | 2 ml |
| Cola essence | 1 ml | 1 ml | 1 ml | 1 ml |
| Distilled water | to 1000 ml*⁴ | to 1000 ml*⁴ | to 1000 ml*⁴ | to 1000 ml*⁴ |

*¹Sweetness ratio, derivative 1:derivative 2:sucrose:Erythritol = 4:4:1:1, PSE 10%, pH 2.8;
*²PSE 10% with derivative 1 alone, pH 2.8;
*³PSE 10% with derivative 2 alone, pH 2.8;
*⁴Addition of distilled water was added to final volume 1000 ml.

1000 ml of each of the above-obtained cola drinks (the product of the present invention, the reference products 1 to 3) was charged into a carbonation bomb, and carbon dioxide gas was charged thereinto. The bomb was stored in the refrigerator for overnight. When it was cooled well, the bomb was opened while it stood still, and the solution thereof was immediately charged into 240 ml can.

(Evaluation of Sweetness Quality)

With respect to the four products obtained above (PSE 10%), the sensory evaluation in terms of the 9 items described above was performed for mutual comparison in the same manner. As a result, compared with the reference product 1 (use of derivative 1 alone) and the reference product 2 (use of derivative 2 alone), the product of the present invention (the mixture of derivative 1, derivative 2, erythritol and sucrose) was improved in the sweetness quality such that the onset of the taste became stronger, and the lingering and astringent tastes became weaker, and thereby the well-balanced taste characteristics was shown and the total taste thereof was preferable (n=20).

Example 25

Production of Sweetener for Tabletop Use

The sweetener was produced by mixing the following components sufficiently.

| Component | Weight | Composition (parts per million, ppm) |
|---|---|---|
| Derivative 2 | 0.70 g | 700 ppm |
| Sucrose | 1000 g | |
| Total amount | 1000.7 g | |

When 1.4 g of the sample obtained were added to 140 ml (volume for the standard coffee cup) of coffee solution, the sweetness intensity of said coffee solution is equivalent to that of PSE 5%. The sweetness ratio of the sweetener is in derivative 2:Sucrose=4:1, and herein the magnification of sweetness intensity of the derivative 2 at PSE 4% was calculated as 6000 times.

1.4 g (/one cup[140 ml]) of the above sweetener for tabletop use was added to coffee, and the coffee was compared to thus obtained coffee with 5 g of sucrose (/one cup[140 ml]) added by the sensory evaluation. There was no significant difference between the sweet tastes of the both, and the coffee using the above sweetener for tabletop use showed a sweetness (sweet taste) similar to that of sucrose with totally preferable taste (n=20).

Example 26

Production of a Grapeade

The grapeades were produced in the following compositions.

| Component | Product of the present invention*[1] | Reference product*[2] |
| --- | --- | --- |
| Derivative 8 | 3.6 mg | 5.5 mg |
| Concentrated grape juice*[3] | 16.7 g | 16.7 g |
| liquid sygar of fructose and glucose*[4] | 17.9 g | — |
| PO-40*[5] | 28.3 g | — |
| Citric acid | 1 g | 1 g |
| Sodium citrate | 0.3 g | 0.3 g |
| DL-malic acid | 1.2 g | 1.2 g |
| Flavor | 1 g | 1 g |
| Distilled water | to 1000 g | to 1000 g |

*[1]Total sweetness ratio; derivative 8:sweetness derived from the concentrated fruit juice:sweetness derived from the liquid sugar of fructose and glucose:sweetness derived from PO-40 = 6.3:1.1:1.8:0.8. The sweetness ratio between derivative 8 and other sweetener with a low intense sweetness is in the ratio of 6.3:3.7.
*[2]Total sweetness ratio; derivative 8:sweetness derived from the concentrated fruit juice = 8.9:1.1
*[3]IRF1/6 (intense sugar 66.9)
*[4]intensity of sweetness 1
*[5]Reduced starch sugar produced by Towa Kasei Co. Ltd., solid component 70%, intensity of sweetness 0.4.

Both products of the present invention and the reference for the above grapeade contain 10% fruit juice, 10% intensity of sweetness (PSE), 16.3 Kcal/100 ml total energy (they can be labeled as "low-calorie" because it is not more than 20 Kcal which is the standard of showing nutrition therefor), and 2.46 g/100 ml sugar (they can be labeled as "low-sugar" because it is lower than 2.5 g/100 ml which is a standard of showing nutrition therefor).

Incidentally, the calculation of the sweetness was made by using the equation for calculating sweetness intensity of derivative 8 (refer to Example 17). When $Y=6.3\%$, $X=0.00036$ g/100 ml, and when $Y=8.9\%$, $X=0.00055$ g/100 ml.

(Evaluation of Sweetness Quality)

With respect to the products (PSE 10%) obtained as described above, the sensory evaluation was performed. As a result, compared with the reference product, the product of the present invention was improved in the sweetness quality such that the onset of the taste became stronger, the lingering taste became weaker, and the astringent and bitter tastes became weaker, and thereby the well-balanced taste characteristics was shown and the total taste thereof was preferable (n=20).

Example 27

Production of an Ice Candy

An ice candy is produced by freezing the aqueous solution of sucrose, fruit juice, thickening agent and flavor. Herein the sweetness (sweet taste) of sucrose was replaced by that of the aspartyl dipeptide ester derivative used in the present invention. As the depression of freezing point of the derivative used in the present invention is smaller than that of sucrose, the freezing point thereof rose by 4 to 5° C. Therefore, it froze easily, it is difficult to prepare without unevenness from freezing, and the surface thereof did not weep ("Naki" in Japanese was not found.). Further, it had a good long time stability for storage. When a fruit flavor was used, the product of good fruit juice flavor was obtained.

The ice candies were produced in the following compositions.

| Component | Product of the present invention*[1] | Reference product*[2] |
| --- | --- | --- |
| Derivative 6 | 6.9 mg | — |
| Sucrose | — | 96.0 g |
| Liquid sugar of fructose and glucose*[3] | 96.0 g | 96.0 g |
| Tartaric acid | 0.5 g | 0.5 g |
| Concentrated orange juice (1/5) | 19.7 g | 19.7 g |
| Xanthan gum | 0.5 g | 0.5 g |
| Carrageenan | 0.5 g | 0.5 g |
| Locust bean gum | 0.5 g | 0.5 g |
| Flavor | 1.5 g | 1.5 g |
| Distilled water | to 1000 g | to 1000 g |

*[1]Total sweetness ratio; derivative 6:sweetness derived from the liquid sugar of fructose and glucose:sweetness derived from concentrated fruit juice (PSE 20.5%) = 4.7:4.7:0.6.
*[2]Total intensity of sweetness: PSE 20.5%
*[3]Intensity of sweetness 1
*[4]IRF1/5.7 (intense sugar 63.6)

Incidentally, the calculation of the sweetness was made by using the equation for calculating sweetness intensity of derivative 6 (refer to Example 17).

When $Y=9.6\%$, $X=0.000685$ g/100 ml.

(Evaluation of Sweetness Quality)

The product of the present invention and the reference product were compared by the sensory evaluation. There was no significant difference between the both sweetnesses thereof, and the product of the present invention gave a preferable taste similar to that of sucrose with totally preferable taste (n=20).

(Third Invention of the Present Invention)

Example 28

With respect to the solution produced by adding derivative 1 (the product of the present invention), or adding nothing (no addition; the reference product) in the concentration shown in the following table 4 to the amino acid solution (2% solution of arginine by weight), the sensory evaluation was performed (using 10 panelists), and the equivalent concentration of bitter taste was determined. The results were shown in the table 4, wherein the equivalent concentration of bitter taste was shown in the concentration of aqueous solution of anhydrous caffeine which is a substance of bitter taste.

TABLE 4

| Sample | Amount of addition (ppm) | Equivalent concentration of bitter taste (g/100 g) |
| --- | --- | --- |
| No addition | — | 0.131 |
| Derivative 1 | 4.4 | 0.060 |

Example 29

With respect to the solution produced by adding derivative 2, Glycyrrhizin or sucrose (the product of the present invention), or adding nothing (no addition; the-reference product) to 2% (by weight) solution of the mixed amino acids (leucine:valine:isoleucine=1:0.5:0.5 by weight), the sensory evaluation was performed (using 10 panelists), and the equivalent concentration of bitter taste was determined in the same way as that described in Example 28, and shown in the table 5.

TABLE 5

| Sample | Amount of addition (ppm) | Equivalent concentration of bitter taste (g/100 g) |
|---|---|---|
| No addition | — | 0.105 |
| Derivative 2 | 10 | 0.051 |
| Glycyrrhizin | 250 | 0.105 |
| Sucrose | 50000 | 0.067 |

Example 30

With respect to the solution produced by adding derivative 4 (2.2 ppm) to each of the substances of Quinine sulfate (39 ppm), anhydrous caffeine (2000 ppm), ferrous citrate (50 ppm), calcium lactate (1500 ppm), and thiamine hydrochloride (5000 ppm) (the product of the present invention), or adding nothing thereto (no addition; the reference product) the reference product (no addition), the sensory evaluation was performed (using 10 panelists), and the equivalent concentration of bitter taste was determined in the same way as that described in Example 28, and shown in table 6.

TABLE 6

| | Equivalent concentration of bitter taste (Amount of anhydrous caffeine g/100 g) | | | | |
|---|---|---|---|---|---|
| | Substance of bitter taste | | | | |
| Sample Component | Quinine sulfate | Caffeine (anhydrous) | Ferrous citarte | Calcium lactate | Tiamine hydrochloride |
| No addition | 0.084 | 0.205 | 0.027 | 0.054 | 0.131 |
| Derivative 4 | 0.025 | 0.045 | 0.020 | 0.025 | 0.093 |

Example 31

Magnification of Sweetness Intensity

For the aspartyl dipeptide ester derivative used in the present invention one having a high intense sweetness, and particularly one having a intense sweetness not less than 4000 times that of sucrose are preferable. Thus, the method of measuring the magnification of sweetness is sown as follows.

An aqueous solution was prepared by diluting derivative 2 to be PSE 10% concentration (15.5 mg/1000 ml=10/6500 g/100 ml), assuming that the intense sweetness of derivative 2 was 6500 times that of sucrose. Separately, aqueous sucrose solutions having sucrose concentrations of (a)6.94%, (b)8.33%, (c)10%, (d)12%, and (e)14.4% were prepared. The sensory evaluation was performed by determining which sucrose solution was closest to the solution of derivative 2 in the sweetness intensity. The result of calculation of the average of points of 20 panelists was 2.25 point.

The sweetness intensity of the solution of derivative 2 was 8.75% according to the following equation: (10.0−8.33)× 0.25+8.33=8.75. Therefore, the magnification of sweetness intensity of derivative 2 was 5600 (=8.75/0.00155) times that of sucrose. When the same experiment was performed, the magnification of sweetness intensity of derivative 1 was 22600 times that of sucrose.

Furthermore, the magnification of sweetness intensity of other derivatives (3 to 9) can be determined by the same method.

And the magnification of sweetness in the cola drink can be also determined by the same method compared to the control solution of cola drink containing 10% sucrose.

The composition of cola drink is as follows.

| Citric acid (crystalline) | 0.25 g/1000 ml |
|---|---|
| Sodium citrate | 0.10 g/1000 ml |
| 85% Phosphoric aid | 0.3 g/1000 ml |
| Cola base | 2 ml/1000 ml |
| Cola essence | 1 ml/1000 ml |
| Sweetener (sample) | Prescribed amount |

As for the concentration of the references, the sucrose concentrations of previous (a) to (e) were used. As a result, the magnification of sweetness intensity in the cola drink of derivative 1 was 22600 times, and that of derivative 2 was 4900 times.

Hereinafter, Production Examples of the aspartyl dipeptide ester derivatives which are used for the present invention are shown.

Production Example 1

Production of Derivative 1

Synthesis of N-[N-[3-(3-hydroxy-4-methoxyphenyl)propyl] L-α-aspartyl]-L-phenylalanine 1-methyl Ester To 485 mg (1.0 mmol) of N-t-butoxycarbonyl-β-o-benzyl-αL-aspartyl-L-phenylalanine methyl ester, 5 ml of a 4N-HCl/dioxane solution were added and stirred at room temperature for one hour. The reaction solution was concentrated under reduced pressure. To the residue were added 30 ml of a 5%-aqueous solution of sodium hydrogen carbonate and extraction was made twice with 30 ml of ethyl acetate. An organic layer was washed with a saturated saline water and dried over anhydrous magnesium sulfate. Magnesium sulfate was filtered off and the liquid filtrate was concentrated under reduced pressure to yield 385 mg of β-o-benzyl-α-L-aspartyl-L-phenylalanine methyl ester, as a viscous oily substance.

385 mg (1.0 mmol) of the above β-o-benzyl-α-L-aspartyl L-phenylalanine methyl ester were dissolved in 15 ml of tetrahydrofuran (THF) to yield a solution which was maintained at 0° C. To this solution were added 268 mg (1.0 mmol) of 3-benzyloxy-4-methoxycinnamaldehyde, 0.060 ml (1.0 mmol) of acetic acid and 318 mg (1.5 mmol) of NaB(OAc)$_3$H and stirred for one hour at 0° C. and overnight at room temperature. To the reaction solution were added 50 ml of a saturated aqueous solution of sodium hydrogen carbonate and extraction was made twice with 30 ml of ethyl acetate. An organic layer was washed with a saturated saline water and dried over anhydrous magnesium sulfate. Magnesium sulfate was filtered off and the liquid filtrate was concentrated under reduced pressure. The residue was purified with preparative thin layer chromatography (PTLC) to yield 523 mg (0.82 mmol) of N-[N-[3-(3-benzyloxy-4-methoxyphenyl) propenyl]-β-o-benzyl-L-α-aspartyl]-L-phenylalanine 1-methyl ester as a viscous oily substance. To above 523 mg (0.82 mmol) of N-[N-[3-(3-benzyloxy-4-methoxyphenyl) propenyl]-β-o-benzyl-L-α-aspartyl]-L-phenylalanine 1-methyl ester were dissolved in a mixed solvent of 30 ml of methanol and 1 ml of water, and 200 mg of 10% palladium carbon (containing 50% of water) were added thereto. The resulting mixture was reduced at room temperature for three hours under a hydrogen atmosphere. The catalyst was filtered off and the filtrate was concentrated under reduced pressure. The residue was purified with PTLC to remove an odor adsorbed to yield 228 mg (0.48 mmol) of N-[N-[3-(3-hydroxy-4-methoxyphenyl) propyl]-L-α-aspartyl]-L-phenylalanine 1-methyl ester as a solid substance.

$^1$HNMR (DMSO-d$_6$) δ:1.50–1.60 (m, 2H), 2.15–2.40 (m,6H), 2.87–2.97 (dd, 1H), 3.05–3.13 (dd, 1H), 3.37–3.43 (m, 1H), 3.62 (s, 3H), 3.71 (s, 3H), 4.50–4.60 (m,1H), 6.52 (d, 1H), 6.60 (s,1H), 6.79 (d, 1H), 7.18–7.30 (m, 5H), 8.52 (d, 1H), 8.80 (brs, 1H).

ESI (Electrospray Ionization)-MS 459.2 (MH$^+$).

Production Example 2

Production of Derivative 2

Synthesis of N-[N-[3-(4-methoxyphenyl)propyl]-L-αaspartyl]-L-phenylalanine 1-methyl Ester 405 mg (2.5 mmol) of 4-methoxycinnamaldehyde, 735 mg (2.5 mmol) of aspartame and 350 mg of 10% palladium carbon (containing 50% of water) were added to a mixed solvent of 15 ml of methanol and 5 ml of water, stirred overnight at room temperature under a hydrogen atmosphere. The catalyst was filtered off and the filtrate was concentrated under reduced pressure. To the residue were added 30 ml of ethyl acetate, stirred for a while and then insoluble materials ware collected by filtration. After washing the collected insoluble materials with a little amount of ethyl acetate, 50 ml of a mixed solvent of ethyl acetate and methanol (5:2) were added to them and they were stirred for a while. Insoluble materials were removed by filtration, and the filtrate was concentrated until all the residue became the solid. This was dried under reduced pressure, and recrystalized in the mixed solvent of methanol and water; to obtain N-[N-[3-(4-methoxyphenyl) propyl]-L-α-aspartyl]-L-phenylalanine 1-methyl ester as a solid with a total yield of 43.4%.

Production Example 3

Production of Derivative 3

Synthesis of N-[N-[3-(3-hydroxy-4-methoxyphenyl)-3-methylbutyl]-L-α-aspartyl]-L-phenylalanine 1-methyl Ester To 703 mg (1.45 mmol) of N-t-butoxycarbonyl-β-o-benzyl-(αL-aspartyl-L-phenylalanine methyl ester, 10 ml of a 4N-HCl/dioxane solution were added and stirred at room temperature for one hour. The reaction solution was concentrated under reduced pressure. To the residue were added 50 ml of a 5%-aqueous solution of sodium hydrogen carbonate and extraction was made twice with 50 ml of ethyl acetate. An organic layer was washed with a saturated saline water and dried over anhydrous magnesium sulfate. Magnesium sulfate was filtered off and the liquid filtrate was concentrated under reduced pressure to yield 557 mg (1.45 mmol) of β-o-benzyl-α-L-aspartyl-L-phenylalanine methyl ester, as a viscous oily substance.

557 mg (1.45 mmol) of the above β-o-benzyl-α-L-aspartyl-L-phenylalanine methyl ester were dissolved in 15 ml of tetrahydrofuran (THF) to yield a solution which was maintained at 0° C. To this solution were added 432 mg (1.45 mmol) of 3-(3-benzyloxy-4-methoxyphenyl)-3-methylbutyl aldehyde, 0.083 ml (1.45 mmol) of acetic acid and 462 mg (2.18 mmol) of NaB(OAc)$_3$H and stirred for one hour at 0° C. and overnight at room temperature. To the reaction solution were added 50 ml of a saturated aqueous solution of sodium hydrogen carbonate and extraction was made twice with 50 ml of ethyl acetate. An organic layer was washed with a saturated saline water and dried over anhydrous magnesium sulfate. Magnesium sulfate was filtered off and the liquid filtrate was concentrated under reduced pressure. The residue was purified with preparative thin layer chromatography (PTLC) to yield 832 mg (1.25 mmol) of N-[N-[3-(3-benzyloxy-4-methoxyphenyl)-3-methylbutyl]-β-o-benzyl-L-α-aspartyl ]-L-phenylalanine 1-methyl ester as a viscous oily substance. To above 832 mg (1.25 mmol) of N-[N-[3-(3-benzyloxy-4-methoxyphenyl)-3-methylbutyl]-β-o-benzyl-L-α-aspartyl ]-L-phenylalanine 1-methyl ester were dissolved in a mixed solvent of 25 ml of methanol and 2 ml of water, and 350 mg of 10% palladium carbon (containing 50% of water) were added thereto. The resulting mixture was reduced at room temperature for three hours under a hydrogen atmosphere. The catalyst was filtered off and the filtrate was concentrated under reduced pressure. The residue was purified with PTLC to remove an odor adsorbed to yield 400 mg (0.82 mmol) of N-[N-[3-(3-hydroxy-4-methoxyphenyl)-3-methylbutyl]-L-α-aspartyl]-L-phenylala nine 1-methyl ester as a solid substance.

$^1$HNMR (DMSO-d$_6$) δ:1.14 (s,6H), 1.54–1.68(m,2H), 2.04–2.22 (m,3H), 2.24–2.34 (dd, 1H), 2.84–2.94 (dd, 1H), 3.00–3.08 (dd, 1H), 3.31–3.36 (m, 1H), 3.59 (s, 3H), 3.71 (s,3H), 4.46–4.55 (m, 1H), 6.60–6.65 (dd, 1H), 6.73 (s, 1H), 6.80 (d, 1H), 7.10–7.28 (m,5H), 8.45 (d, 1H), 8.75 (brs, 1H).

ESI-MS 487.3 (MH$^+$)

Production Example 4

Production of Derivative 4

Synthesis of N-[N-[3-(3-methyl-4-hydroxyphenyl)-3-methylbutyl]-L-α-aspartyl]-L-phenylalani ne 1-methyl Ester N-[N-[3-(3-methyl-4-hydroxyphenyl)-3-methylbutyl]-L-α-aspartyl]-L-phe nylalanine 1-methyl ester was obtained as a solid substance, with a total yield of 63.2%, in the same way as in Production Example 3, except using 3-(3-methyl-4-benzyloxyphenyl)-3-methylbutyl aldehyde in place of 3-(3-benzyloxy-4-methoxyphenyl)-3-methylbutyl aldehyde.

$^1$HNMR (DMSO-d$_6$) δ:1.14 (s,6H), 1.59–1.68 (m,2H), 2.09 (s,3H), 2.09–2.18 (m,3H), 2.25 (dd,1H), 2.90 (dd,1H), 3.02 (dd,1H), 3.30–3.36 (m,1H), 3.59 (s,3H), 4.46–4.54 (m,1H), 6.68 (d,1H), 6.88 (dd,1H), 6.96 (s,1H), 6.14–6.73 (m,5H), 8.46 (d,1H), 9.01 (brs, 1H).

ESI-MS 471.4 (MH$^+$)

Production Example 5

Production of Derivative 5

Synthesis of N-[N-[3-(4-methoxyphenyl)-3-methylbutyl]-L-α-aspartyl]-L-phenylalanine 1-methyl Ester N-[N-[3-(4-methoxyphenyl)-3-methylbutyl]-L-α-aspartyl]-L-phenylalanin e 1-methyl ester was obtained as a solid substance, with a total yield of 72.2%, in the same way as in Production Example 3, except using 3-(4-methoxyphenyl)-3-methylbutyl aldehyde in place of 3-(3-benzyloxy-4-methoxyphenyl)-3-methylbutyl aldehyde.

$^1$HNMR (DMSO-d$_6$) δ:1.17 (s, 6H), 1.62–1.72 (m,2H), 2.04–2.20 (m, 3H), 2.24–2.34 (dd, 1H), 2.84–2.94 (dd, 1H), 2.95–3.07 (dd,1H), 3.30–3.35 (m, 1H), 3.51 (s, 3H), 3.70 (s,3H), 4.46–4.54 (m,1H), 6.83 (d,2H), 7.14–7.28 (m, 7H), 8.43 (d, 1H).

ESI-MS 471.3 (MH$^+$)

Production Example 6

Production of Derivative 6
Synthesis of N-[N-[3-(4-hydroxyphenyl)-3-methylbutyl]-L-α-aspartyl]-L-phenylalanine 1-methyl Ester N-[N-[3-(4-hydroxyphenyl)-3-methylbutyl]-L-α-aspartyl]-L-phenylalanine 1-methyl ester was obtained as a solid substance, with a total yield of 64.5%, in the same way as in Production Example 3, except using 3-(4-benzyloxyphenyl)-3-methylbutyl aldehyde in place of 3-(3-benzyloxy-4-methoxyphenyl)-3-methylbutyl aldehyde.

$^1$HNMR (DMSO-$d_6$) δ:1.15 (s, 6H), 1.58–1.72 (m,2H), 2.04–2.20 (m, 3H), 2.24–2.34 (dd, 1H), 2.85–2.94 (dd, 1H), 3.00–3.08 (dd,1H), 3.30–3.36 (m, 1H), 3.59 (s, 3H), 4.46–4.55 (m,1H), 6.67 (d,2H), 7.07 (d, 2H), 7.10–7.27 (m, 5H), 8.44 (d, 11H), 9.15 (brs,1H).

ESI-MS 457.3 (MH$^+$)

Production Example 7

Production of Derivative 7
Synthesis of N-[N-[3-(2-hydroxy-4-methoxyphenyl) propyl]-L-α-aspartyl]-L-phenylalanine 1-methyl Ester N-[N-[3-(2-hydroxy-4-methoxyphenyl) propyl]-L-α-aspartyl]-L-phenylalanine 1-methyl ester was obtained as a solid substance, with a total yield of 54.4%, in the same way as in Production Example 1, except using 2-benzyloxy-4-methoxycinnamaldehyde in place of 3-benzyloxy-4-methoxycinnamaldehyde.

$^1$HNMR (DMSO-$d_6$) δ: 1.52–1.57 (m,2H), 2.20–2.31 (m, 2H), 2.26–2.41 (m, 4H), 2.88–3.11 (m, 2H), 3.41–3.43 (m, 1H), 3.62 (s, 3H), 3.65 (s, 3H), 4.53–4.59 (m,1H), 6.28–6.36 (m, 2H), 6.88–6.90 (d,1H), 7.19–7.29 (m, 5H), 8.55 (d, 1H).

ESI-MS 459.3 (MH$^+$)

Production Example 8

Production of Derivative 8
Synthesis of N-[N-[3-(3-methyl-4-hydroxyphenyl) propyl]-L-α-aspartyl]-L-phenylalanine 1-methyl Ester N-[N-[3-(3-methyl-4-hydroxyphenyl) propyl]-L-α-aspartyl]-L-phenylalanine 1-methyl ester was obtained as a solid substance, with a total yield of 32.2%, in the same way as in Production Example 1, except using 3-methyl-4-benzyloxycinnamaldehyde in place of 3-benzyloxy-4-methoxycinnamaldehyde.

$^1$HNMR (DMSO-$d_6$) δ: 1.50–1.58 (m,2H), 2.08 (s, 3H), 2.09–2.30 (m, 2H), 2.26–2.38 (m, 4H), 2.89–3.09 (m, 2H), 3.35–3.42 (m, 1H), 3.62 (s, 3H), 4.54–4.59 (m,1H), 6.65–6.83 (m, 3H), 7.19–7.28 (m, 5H), 8.52 (d, 1H), 9.04 (brs, 1H).

ESI-MS 443.4 (MH$^+$)

Production Example 9

Production of Derivative 9
Synthesis of N-[N-[3-(2,4-dihydroxyphenyl) propyl]-L-α-aspartyl]-L-phenylalanine 1-methyl Ester N-[N-[3-(2,4-dihydroxyphenyl) propyl]-L-α-aspartyl]-L-phenylalanine 1-methyl ester was obtained as a solid substance, with a total yield of 42.6%, in the same way as in-Production Example 1, except using 345 mg (1.0 mmol) of 3-(2,4-dibenzyloxyphenyl)-2-propenylaldehyde in place of 268 mg (1.0 mmol) of 3-benzyloxy-4-methoxycinnamaldehyde.

ESI-MS 445.3 (MH$^+$)

Effect of the Invention

According to the present invention, the sweetener composition with a high intense sweetness having a well-balanced taste of good quality, which cannot be obtained in a single use of the derivative represented by said general formula (2), particularly the general formula (1), by using at the same time therewith or mixing therewith the another sweetener with a high intense sweetness used in said present invention (the first invention) or the sugar and so on used in said present invention (the second invention) can be provided. It can be used as a sweetener and an agent for imparting sweetness for food and drink and so on. For example, it exhibits superiority in the use for cola drink such as a carbonated cola and so on, and can be applicable widely for all products which is in need of sweetness without limitation to such use.

According to another embodiment of the present invention (the third invention), it was confirmed that an effect of correcting a taste with masking effect or another effect, that is an effect of removing or suppressing a bitter taste is shown by mixing the aspartyl dipeptide ester derivative(s) (one or more) represented by said general formula (2), particularly the general formula (1), to a substance of bitter taste or a product containing it and having the bitter taste for use, and further that the effect can be maintained for a long time, and these derivatives are superior as a taste modifier. Therefore, the taste modifier of another embodiment of the present invention (the third invention) can be used as a taste modifier for food and drink in need of the taste correction and a medicine and so on. Particularly, it is preferable in view of maintenance of the effect for a long time in the form of the solution.

What is claimed is:

1. A composition, comprising an aspartyl dipeptide ester compound represented by formula (1) or a salt thereof and another high intensity sweetener in an amount sufficient to improve the quality of the sweetness of said aspartyl dipeptide ester compound:

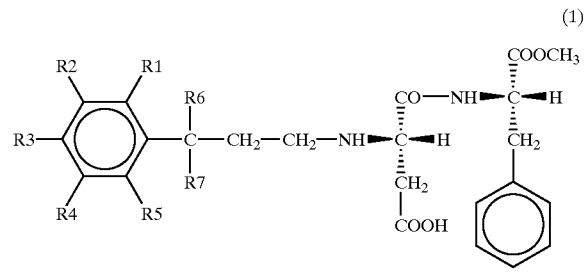

(1)

wherein $R_3$ is selected from the group consisting of a hydrogen atom, a hydroxyl group, a methoxy group and a methyl group, wherein a) when $R_3$ is a hydroxyl group, $R_1$ and $R_5$ are independently selected from the group consisting of a hydrogen atom, a hydroxyl group, a methoxy group and a methyl group, $R_2$ and $R_4$ are independently selected from the group consisting of a hydrogen atom, a hydroxyl group, and a methyl group, and $R_6$ and $R_7$ are independently a hydrogen atom or a methyl group;

b) when $R_3$ is a methoxy group, $R_1$, $R_2$, $R_4$, and $R_5$ are independently selected from the group consisting of a hydrogen atom, a hydroxyl group, a methoxy group and a methyl group, and $R_6$ and $R_7$ are independently a hydrogen atom or a methyl group; and c) when $R_3$ is a hydrogen atom or a methyl group, $R_1$, $R_2$, $R_1$, and $R_5$ are independently selected from the group consisting of a hydrogen atom, a hydroxyl group, a methoxy group and a methyl group, and $R_6$ and $R_7$ are independently a hydrogen atom or a methyl group so long as at least one of $R_1$, $R_2$, $R_4$, and $R_5$ is a hydroxyl group or a methoxy group;

and when $R_6$ and $R_7$ are different substituents, the carbon atom to which these substituents are linked is in the (R), (S) or (RS) configuration.

2. The composition as defined in claim 1, wherein the sweetness intensity of said aspartyl dipeptide ester compound is more than 4,000 times that of sucrose.

3. The composition as defined in claim 2, wherein $R_3$ is a hydroxyl group or a methoxy group; and $R_4$ and $R_5$ are hydrogen atoms.

4. The composition as defined in claim 3, wherein $R_1$ is a hydroxyl group.

5. The composition as defined in claim 3, wherein $R_1$ is a hydrogen atom.

6. The composition as defined in claim 4, wherein $R_2$, $R_6$ and $R_7$ are hydrogen atoms.

7. The composition as defined in claim 5, wherein $R_2$ is a hydrogen atom, a hydroxyl group or a methyl group.

8. The composition as defined in claim 1, wherein the aspartyl dipeptide ester compound is selected from the group consisting of: (1) a compound wherein $R_1$, $R_4$, $R_5$, $R_6$, and $R_7$ are hydrogen, $R_2$ is OH, $R_3$ is $OCH_3$; (2) a compound wherein $R_1$, $R_2$, $R_4$, $R_5$, $R_6$, and $R_7$ are hydrogen, $R_3$ is $OCH_3$; (3) a compound wherein $R_1$, $R_4$, and $R_5$, are hydrogen, $R_2$ is OH, $R_3$ is $OCH_3$, $R_6$ and $R_7$ are $CH_3$; (4) a compound wherein $R_1$, $R_4$, and $R_5$ are hydrogen, $R_2$ is $CH_3$, $R_3$ is OH, $R_6$ and $R_7$ are $CH_3$; (5) a compound wherein $R_1$, $R_2$, $R_4$, and $R_5$ are hydrogen, $R_3$ is a $OCH_3$, $R_6$ and $R_7$ is $CH_3$; (6) a compound wherein $R_1$, $R_2$, $R_4$, and $R_5$ are hydrogen, $R_3$ is OH, $R_6$ and $R_7$ is $CH_3$; (7) a compound wherein $R_1$ is OH, $R_2$, $R_4$, $R_5$, $R_6$ and $R_7$ are hydrogen, $R_3$ is a $OCH_3$; (8) a compound wherein $R_1$, $R_4$, $R_5$, $R_6$, and $R_7$ are hydrogen, $R_2$ is a $CH_3$, $R_3$ is OH; and (9) a compound wherein $R_1$ and $R_3$ are OH, $R_2$, $R_4$, $R_5$, $R_6$ and $R_7$ are hydrogen.

9. The composition as defined in claim 8, wherein the aspartyl dipeptide ester compound is a compound wherein $R_1$, $R_2$, $R_4$, $R_5$, $R_6$, and $R_7$ are hydrogen, $R_3$ is $OCH_3$ and said another high intensity sweetener is Aspartame, wherein the ratio of said Aspartame to the total amount of said compound is from 25 to 99.7% by weight.

10. The composition as defined in claim 1, wherein said another high intensity sweetener is at least one sweetener selected from the group consisting of Aspartame, Acesulfame K, Saccharine, a salt of Saccharine, Sodium cyclamate, sucralose, disodium glycyrrhizinate, Alitame, Glycyrrhizin, a Stevioside compound, and Thaumatin.

11. The composition as defined in claim 1, wherein said another high intensity sweetener is Aspartame.

12. The composition as defined in claim 11, wherein said Aspartame is in an amount of from 5 to 90% by sweetness intensity, relative to a total amount of the aspartyl dipeptide ester derivative.

13. The composition as defined in claim 1, wherein said aspartyl dipeptide ester is in an amount of from 1 to 99.9% by weight.

14. A product in need of sweetening, comprising the composition as defined in claim 1 in an amount to sweeten said product.

15. The product as defined in claim 14, which is selected from the group consisting of a food, a beverage, and a medicinal product.

16. The product as defined in claim 14, wherein said product is a cola drink.

17. A method of imparting a sweet taste into a product in need of sweetening, comprising adding the composition as defined in claim 1 to said product in an amount to impart a sweet taste into said product.

* * * * *